United States Patent [19]
Pamukcu et al.

[11] Patent Number: 6,034,099
[45] Date of Patent: Mar. 7, 2000

[54] METHOD FOR INHIBITING NEOPLASTIC LESIONS BY ADMINISTERING 4-(ARYLMETHYLENE)- 2, 3- DIHYDRO-PYRAZOL-3-ONES

[75] Inventors: Rifat Pamukcu, Spring House; Gary A. Piazza, Doylestown, both of Pa.

[73] Assignee: Cell Pathways, Inc., Horsham, Pa.

[21] Appl. No.: 09/200,136

[22] Filed: Nov. 24, 1998

[51] Int. Cl.⁷ .................................................. A01N 43/42
[52] U.S. Cl. ....................... 514/310; 514/313; 548/368.1; 548/368.7
[58] Field of Search ................... 514/310, 313; 548/368.1, 368.7

[56] References Cited

U.S. PATENT DOCUMENTS

| | | |
|---|---|---|
| 3,031,450 | 4/1962 | Fischer et al. . |
| 3,161,654 | 12/1964 | Shen . |
| 3,322,755 | 5/1967 | Roch et al. . |
| 3,517,005 | 6/1970 | Cronin et al. . |
| 3,594,480 | 7/1971 | Cronin et al. . |
| 3,647,858 | 3/1972 | Hinkley et al. . |
| 3,654,349 | 4/1972 | Shen et al. . |
| 3,780,040 | 12/1973 | Schnettler et al. . |
| 3,812,127 | 5/1974 | Cronin et al. . |
| 3,819,631 | 6/1974 | Broughton et al. . |
| 3,865,840 | 2/1975 | Carson . |
| 3,920,636 | 11/1975 | Takahasi et al. . |
| 4,001,237 | 1/1977 | Partyka et al. . |
| 4,001,238 | 1/1977 | Partyka et al. . |
| 4,039,544 | 8/1977 | Broughton et al. . |
| 4,060,615 | 11/1977 | Matier et al. . |
| 4,076,711 | 2/1978 | Ganguly et al. . |
| 4,079,057 | 3/1978 | Juby et al. . |
| 4,098,788 | 7/1978 | Crenshaw et al. . |
| 4,101,548 | 7/1978 | Crenshaw et al. . |
| 4,102,885 | 7/1978 | Crenshaw et al. . |
| 4,138,561 | 2/1979 | Crenshaw et al. . |
| 4,146,718 | 3/1979 | Jenks et al. . |
| 4,161,595 | 7/1979 | Kaplan et al. . |
| 4,171,363 | 10/1979 | Crenshaw et al. . |
| 4,208,521 | 6/1980 | Crenshaw et al. . |
| 4,423,075 | 12/1983 | Dvornik et al. . |
| 4,457,927 | 7/1984 | Biere et al. . |
| 4,460,590 | 7/1984 | Möller . |
| 4,460,591 | 7/1984 | DeGraw et al. . |
| 4,880,810 | 11/1989 | Lowe, III et al. . |
| 4,885,301 | 12/1989 | Coates . |
| 4,923,874 | 5/1990 | McMahon et al. . |
| 4,971,972 | 11/1990 | Doll et al. . |
| 5,073,559 | 12/1991 | Coates . |
| 5,091,431 | 2/1992 | Tulshian et al. . |
| 5,147,875 | 9/1992 | Coates et al. . |
| 5,175,151 | 12/1992 | Afonso et al. . |
| 5,223,501 | 6/1993 | Chakravarty et al. . |
| 5,250,535 | 10/1993 | Verheyden et al. . |
| 5,254,571 | 10/1993 | Coates et al. . |
| 5,358,952 | 10/1994 | Moschel et al. . |
| 5,376,683 | 12/1994 | Klar et al. . |
| 5,393,755 | 2/1995 | Neustadt et al. . |
| 5,401,774 | 3/1995 | Pamukcu et al. . |
| 5,439,895 | 8/1995 | Lee et al. . |
| 5,488,055 | 1/1996 | Kumar et al. . |
| 5,614,530 | 3/1997 | Kumar et al. . |
| 5,614,627 | 3/1997 | Takase et al. . |
| 5,696,159 | 12/1997 | Gross et al. . |
| 5,728,563 | 3/1998 | Tanaka . |
| 5,756,818 | 5/1998 | Buchmann et al. . |
| 5,852,035 | 12/1998 | Pamukcu et al. . |
| 5,858,694 | 1/1999 | Piazza et al. . |
| 5,874,440 | 2/1999 | Pamukcu et al. . |

FOREIGN PATENT DOCUMENTS

| | | |
|---|---|---|
| 0 330 004 A1 | 6/1989 | European Pat. Off. . |
| 0 347 146 A2 | 12/1989 | European Pat. Off. . |
| 0 349 239 A2 | 1/1990 | European Pat. Off. . |
| 0 351 058 | 1/1990 | European Pat. Off. . |
| 0 352960 A2 | 1/1990 | European Pat. Off. . |
| 0 395328 A2 | 10/1990 | European Pat. Off. . |
| 0 428268 A2 | 5/1991 | European Pat. Off. . |
| 0 463756 A1 | 1/1992 | European Pat. Off. . |
| 0 508586 A1 | 10/1992 | European Pat. Off. . |
| 0 526004 A1 | 2/1993 | European Pat. Off. . |
| 0 607439 A1 | 7/1994 | European Pat. Off. . |
| 0 722937 A1 | 7/1996 | European Pat. Off. . |
| 0 743304 A1 | 10/1996 | European Pat. Off. . |
| 3038166 | of 1981 | Germany . |
| 274218 | 12/1989 | Germany . |
| 56-53659 | 5/1981 | Japan . |
| 57-167974 | 10/1982 | Japan . |
| 8-311035 | 11/1996 | Japan . |
| 807826 | 1/1959 | United Kingdom . |
| 2063249 | 6/1981 | United Kingdom . |
| WO 92/03419 | 3/1992 | WIPO . |
| WO 93/07149 | 4/1993 | WIPO . |
| WO 93/12095 | 6/1993 | WIPO . |
| WO 94/05661 | 3/1994 | WIPO . |
| WO 94/19351 | 9/1994 | WIPO . |
| WO 94/29277 | 12/1994 | WIPO . |
| WO 95 18969 | 7/1995 | WIPO . |
| WO 95/26743 | 10/1995 | WIPO . |
| WO 97/03070 | 1/1997 | WIPO . |
| WO 97/03985 | 2/1997 | WIPO . |
| WO 97/24334 | 7/1997 | WIPO . |
| WO 98/14448 | 4/1998 | WIPO . |
| WO 98/15530 | 4/1998 | WIPO . |
| WO 98/16224 | 4/1998 | WIPO . |
| WO 98/16521 | 4/1998 | WIPO . |
| WO 98/17668 | 4/1998 | WIPO . |
| WO 98/08848 | 5/1998 | WIPO . |
| WO 98/23597 | 6/1998 | WIPO . |
| WO 98/38168 | 9/1998 | WIPO . |
| WO 96/32379 | 10/1998 | WIPO . |

OTHER PUBLICATIONS

Waddell, W.R. et al., Am. J. Surgery, vol. 157, pp. 175–179 (1989).

Gonzaga, R.A.F. et al., The Lancet, Mar. 30, 1985, p. 751.

Waddell, W.R. et al., J. Surg. Oncology, vol. 24, pp. 83–87 (1983).

Federation Proceedings (1972) of the Federation of American Societies for Experimental Biology abstract Nos. 2044 and 2045.

(List continued on next page.)

*Primary Examiner*—James O. Wilson
*Assistant Examiner*—Howard Owens
*Attorney, Agent, or Firm*—Robert W. Stevenson

[57] ABSTRACT

A method for treating neoplasia involving the administration of certain pyrazolinone derivatives.

9 Claims, No Drawings

OTHER PUBLICATIONS

Gilman, S.C. et al., Nonsteroidal Anti–inflammatory Drugs in Cancer Therapy, (circa 1985).

Brogden, R.N. et al., Drugs, vol. 16, pp. 97–114 (1978).

Hucker, H.B. et al., Drug Metabolism & Disposition, vol. 1, No. 6, pp. 721–736 (1973).

Shen, T.Y. et al., Chemical and Biological Studies on Indomethacin, Sulindac and Their Analogs, pp. 107–178 (circa 1975).

Duggan, D.E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

Glavin, G.B. et al., Toxicology and Applied Pharmacology, vol. 83, pp. 386–389 (1986).

Moorghen, M. et al., Journal of Pathology, vol. 156, pp. 341–347 (1988).

Moorghen, M. et al., Acta Histochemica, Suppl.–Band XXXIX, S. 195–199 (1990).

Bjarnason et al., Gastroenterology, vol. 94, No. 4, pp. 1070–1074 (1988).

Badrich, Y., et al., Chem. Ber., vol. 125, pp. 667–674 (1992).

Silvola, J. et al., Effects of nonsteroidal anti–inflammatory drugs on rat gastric mucosal phosphodiesteraseactivity, Agents and Actions, vol. 12.4, pp. 516–520 (1982).

Curtis–Prior, P.B. et al., Cyclic Nucleotide Phosphodiesterase Activity of Human Normal and Carcinomatous Lung Tissue, The Lancet, pp. 1225–1225 Dec. 4, 1976.

Pepin, P. et al., Effects of Sulindac oand Oltipraz on the tumorigenicity of 4–(methylnitrosamino)1–(3–pyridyl)–1–Butanone in A/J mouse lung, Carcinogenesis, vol. 13, No. 3, pp. 341–348 (1992).

Nicholson, C.D. et al. Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Turner, N.C. et al., Relaxation of guinea–pig trachea by cyclic AMP phosphodiesterase inhibitors and their enhancement of sodium mitroprusside, Br. J. Pharmacol. vol. III, pp. 1047–1052 (1994).

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guinea–pig, Br. J. Pharmacol., vol. 111, 1198–1204 (1994).

Ferreira, S.H. et al., The molecular mechanism of action of peripheral morphone analgesia: stimulation of the cGMP system via nitric oxide release, European Journal of Pharmacol., 201, pp. 121–122 (1991).

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphordiesterase Activity of Carboxylic Acid Mimetics of Cyclic Guanosine 3",5"–Monophosphate, J. Med. Chem, vol. 36, 1210–1220 (1993).

Yasumotot, T. et al., Properties of Base–Substituted and Carboxyl–Esterifeid Analogues of Griseolic Acid, a Potent cAMP Phosphdiesterase Inhibitor, Biochemical Pharamacology, vol. 43, No. 10, pp. 2073,2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al., Effect of Mopidamol on Survival in Carcinoma of the Lung and Colon: Final Report of Veterans Administration Cooperative Study No. 188, J. of the Nat'l Cancer Inst., vol. 80, No. 2, pp. 90–96 (1988).

Lichtner, R. B. et al., The Pyrimido–pyrimidine Derivatives RA 233 adn RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954, (Jun., 1980).

Bergstrand, Hakan et al., Effects of Antiallergic Agents, Compound 48/80, and Some Reference Inhibitors on the Activity of Partially Purified Human Lung Tissue Adenosine Cyclic 3',5'–Monophosphate and Guanosine Cyclic 3',5'–Monophosphate Phosphodiesterses, Molecular Pharmacology, 13, pp. 38–43 (1976).

Drees, Markus et al., 3',5'–Cyclic Nucleotide Phosphodiesterase in Tumor Cells as Potential Target for TUmor Growth Inhibition, Cancer Research 53, pp. 3058–3061 (1993).

Semmler, J. et al., Xanthine derivatives: comparison between suppression of tumor necrosis factor–x production and inhibition of cAMP phosphodiesterase activity, Immunology 78, pp. 520–525 (1993).

Mehta, Rajendra et al., Structure–Activity Relationships of Brassinin in Preventing the Development of Carcinogen–Induced Mammary Lesions in Organ Culture, Anticancer Research 14: 1209–1214 (1994).

Makaryan, A.P. et al., Cyclic Nucleotides in Patients with Malignant Neoplasms of the Colon, Laboratornoe Delvo, vol. 8, pp. 31–33 (1991).

Carter et al., Chemotherapy of Cancer, $2^{nd}$Ed., John Wiley & Sons, NY, NY, 1981, pp. 362–365.

Biddle, William et al., Antieoplastic Effect of the Pyrimido–Pyrimidine Derivative: RA 233, Pathologic Biologie, Jan., 1984, pp. 9–13.

Clarke, W.R. et al., The type III phosphodiesterase inhibitor milrinone and type V PDE inhibitior dipyridamole individually and synergistically reduce elevated pulmonary vascular resistance (Abstract Only), Pulm. Pharmacol., 7(2), pp. 81–89, (1994).

Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–1151 (1993).

Marcoz, P. et al., Modulationof rat thymocyte proliferative response through the inhibition of different cyclic nucleotide phosphodiesterase isoforms by means of selective inhibitors and cGMP–elevating agents (Abstract Only), Mol. Pharmacol. 44(5), pp. 1027–1035 (1993).

Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Giorgi, Mauro et al., Characterization of 3':5' cyclic nucleotide phosphodiesterase activities of mouse neuroblastoma N18TG2 cells (Abstract Only), FEBS Lett. 324(1) pp. 76–80 (1993).

Porter, Roderick et al., Preparation of 6–phenyl–3–(5–tetrazoly)pyridin–2–(H)–one derivatives as cyclic AMP–dependent protein kinase agonists (Abstract Only), PCT Int. Appl. WO9206085 A1, (Sep. 26, 1991).

Molnar–Kimber, K. L. et al., Differential regulation of TNF–a and IL–1B production from endotoxin stimulated human monocytes by phosphodiesterase inhibitors (Abstract Only), Mediators Inflammation 1(6) pp. 411–417 (1992).

Radomski, Marek W. et al., Human Colorectal adenovcarcinoma cells: different nitric oxide synthesis determines their ability of aggregate platelets (Abstract Only), Cancer REs. 51(22) pp. 6073–6078 (1991).

Anderson, Thomas L. G. et al., Interactions between isoprenalie, sodium nitroprusside, and isozyme–selective phosphodiesterase inhibitors on ADP–induced aggregation and cyclic Nucleotide levels in human platelets (Abstract Only), J. Cardiovasc. Pharmacol. 18(2) pp. 237–242 (1991).

Souness, John E. et al., Role of Selective cyclic GMP phosphodiesterase inhibition in the myorelaxant actions of M&B 22,943, MY–5445, vinpocetine and 1–methyl–3–isobutyl–8–(methylamino)xanthine (Abstract Only), Br. J. Pharmacol. 98(3) pp. 725–734 (1989).

Lichtner, Rosemarie B. The pyrimidopyrimidine derivatives RA233 and RX–RA85 affect cell cycle distribution of two murine tumor cell lines (Abstract Only), Eur. J. Cancer Clin. Oncol. 25(6) pp. 945–951 (1989).

Mamytbekova, A., et al., Antimetastatic effect of flurbiprofen and other platelet aggregation inhibitors (Abstract Only), Neoplasma 33(4), pp. 417–421 (1986).

Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).

Guanosine Monophosphate Phosphodiesterases with Oral Antihypertensive Activity, J. Med. Chem. 1997, 40, pp. 2196–2210.

J.A. Mitchell et al., Selectivity of nonsteroidal antiinflammatory drugs as inhibitors of constitutive and inducible cyclooxygenase; Proc. Natl. Acad. Sci. USA, vol. 90, Dec. 1994, pp. 11693–11697.

J.D. Gaffen et al.: Increased killing of malignant cells by giving indomethacin with methotrexate, p. 30; column 1; XP002084860Chemical Abstract, vol. 106, No. 11, Mar. 16, 1987, abstract no. 78377, J.D.

Tsou, K–C. et al. 5'–Nucleotide Phosphodiesterase Isozyme–V as a Marker for Liver Metastases in Breast Cancer Patients, Cancer 54:1788–1793, 1984.

Epstein P M et al.; Dep. Pharmacol., Univ. Tex. Med. Sch., M.D. Anderson Hosp., Houston, Tex. 88030, USA BIOSIS 78:140912, Increased Cyclic Nucleotide PhosphoDi Esterase Activity Associated With Proliferation and Cancer in Human and Murine Lymphoid Cells.

Christian Schudt et al., "Phosphodiesterase Inhibitors" The Handbook of Immunopharmacology, Academic Press, 1996, pp. 65–134.

METHOD FOR INHIBITING NEOPLASTIC LESIONS BY ADMINISTERING 4-(ARYLMETHYLENE)- 2, 3- DIHYDRO-PYRAZOL-3-ONES

TECHNICAL FIELD

This invention relates to a method for the selective inhibition of neoplastic cells, for example, for the treatment or prevention of precancerous lesions or other neoplasias in mammals.

BACKGROUND OF THE INVENTION

Each year in the United States alone, untold numbers of people develop precancerous lesions, which is a form of neoplasia, as discussed below. Such lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds that prevent or induce the remission of existing precancerous or cancerous lesions or carcinomas would greatly reduce illness and death from cancer.

For example, approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

In the breast, breast cancer is often treated surgically, often by radical mastectomy with its painful aftermath. Such surgery is costly, too.

As indicated above, each lesion carries with it a chance that it will develop into a cancer. The likelihood of cancer is diminished if a precancerous lesion is removed. However, many of these patients demonstrate a propensity for developing additional lesions in the fixture. They must, therefore, be monitored periodically for the rest of their lives for reoccurrence.

In most cases (i.e. the cases of sporadic lesion formation, e.g. so-called common sporadic polyps), lesion removal will be effective to reduce the risk of cancer. In a small percentage of cases (i.e. cases where numerous lesions form, e.g. the so-called polyposis syndromes), removal of all or part of the effected area (e.g. the colon) is indicated. For example, the difference between common sporadic polyps and polyposis syndromes is dramatic. Common sporadic polyp cases are characterized by relatively few polyps which can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each lesion carries with it a palpable risk of cancerous development, patients who form many lesions (e.g. polyposis syndrome patients) invariably develop cancer if left untreated. Surgical removal of the colon is the conventional treatment in polyposis patients. Many polyposis patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because chemotherapy for cancer itself is often not effective and has severe side effects. Cancer chemoprevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those patients with high-risk genetic factors, such as the potential for polyposis syndrome, who would greatly benefit from chemopreventative drugs. Therefore, finding such anti-cancer drugs that can be used for prolonged preventive use is of vital interest.

Known chemopreventative and chemotherapeutic drugs are believed to kill cancer cells by inducing apoptosis, or as sometimes referred to as "programmed cell death." Apoptosis naturally occurs in virtually all tissues of the body, and especially in self-renewing tissues such as bone marrow, immune cells, gut, liver and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis play a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long-term use, or use in otherwise healthy individuals with precancerous lesions. These side effects, which are a result of the high levels of cytotoxicity of the drugs, include hair loss, weight loss, vomiting, immune suppression and other toxicities. Therefore, there is a need to identify new drug candidates for therapy that do not have such serious side effects in humans.

In recent years, several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the prophylactic use of currently available NSAIDs, even in polyposis syndrome patients, is marked by severe side reactions that include gastrointestinal irritations, perforations, ulcerations and kidney toxicity. Once NSAID treatment is terminated due to such complications, the polyps return, particularly in polyposis syndrome patients.

Sulindac has been particularly well received among the NSAEDs for the polyp treatment. Sulindac is a sulfoxide compound that itself is believed to be inactive as an anti-arthritic agent. The sulfoxide is reportedly converted by liver enzymes to the corresponding sulfide, which is acknowledged to be the active moiety as a prostaglandin synthesis inhibitor. The sulfide, however, is associated with the side effects of conventional NSAIDs. The sulfoxide is also known to be metabolized to sulfone compound that has been found to be inactive as an inhibitor of prostaglandin synthesis but active as an inhibitor of precancerous lesions.

SUMMARY OF THE INVENTION

This invention includes a method of inhibiting neoplastic cells by exposing those cells to a pharmacologically effective amount of those compounds described below. Such compounds are effective in modulating apoptosis and eliminating and inhibiting the growth of neoplasias such as precancerous lesions, but are not characterized by the severe side reactions of conventional NSAIDs or other chemotherapeutics.

The compounds of that are useful in the methods of this invention include those $\Delta^2$ pyrazolinone-5-derivatives of Formula I.

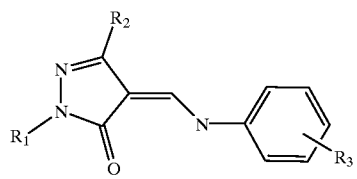

formula I wherein $R_1$ is tetrazolyl- or phosphonyl-substituted phenyl, pyridyl, or a substituted or unsubstitued benzyl, phenyl, or alkoxybenzyl (wherein said alkoxybenzyl has 1–3 carbons in the alkyl chain), wherein said substituents (on said benzyl, phenyl or alkoxybenzyl) are one to three selected from the group consisting of amino, acyl, halogen, nitro, CN, AO—, carboxyl, sulfonyl, A—O—CO—, A—CO—NH—, A—CO—NA—, carbamoyl, N-alkylcarbamoyl, N,N-dialkylcarbamoyl (with 1–6 carbons in the alkyl chain), A—O—CO—NH—, A—O—CO—NA—, $R_4NSO_2R_5$ or $SO_2NR_4R_5$;

$R_2$ is selected from the group consisting of $C_{1-5}$ alkyl, alkoxycarbonylalkyl, hydroxyalkyl, and hydroxycarbonylalkyl;

$R_3$ is hydrogen, $C_{1-5}$ alkyl, $C_{1-5}$ alkoxy, halo-substituted alyl, arninoalkanoyl, aminoalkyl, carbamoyl, $SO_2NR_4R_5$;

$R_4$ and $R_5$ are independently hydrogen or $C_{1-6}$ alkyl, or —$NR_4R_5$ together form a 5 or 6 membered ring optionally containing other heteroatoms selected from N, S, O, which ring can be optionally substituted by A, A—CO—NH—$SO_2$—, A—CO—NA—$SO_2$—, A—$SO_2$—NH—, A—$SO_2$—NA—, (A—$SO_2)_2N$—, and A is $C_{1-6}$ alkyl, $C_{1-6}$ haloalkyl; and physiologically acceptable salts thereof.

Preferred compounds useful in the practice of this invention are those of Formula I wherein:

$R_1$ is a defined above;

$R_2$ is $H_5C_2$—O—CO—$CH_2$, and $R_3$ is aminoalkanoyl, alkanoylamino, carbamoyl, $SO_2NR_4R_5$; and $R_4$ and $R_5$ are independently selected from hydrogen or $C_{1-6}$ alkyl, or $NR_4R_5$ together form a 5 or 6 membered ring optionally containing other heteroatoms selected from N, S, O, which ring can be optionally substituted by A; and physiologically acceptable salts thereof. In particular the compounds:

N-3-(4-(2-Ethylanilinomethylene)-4,5-dihydro-3-methyl-5-oxo-1H-pyrazol-1-yl)-phenyl)-carbamic acid methylester 4-((2-Ethoxyanilinomethylene)-4,5-dihydro-3-methyl-5-oxo-1H-pyrazol-1-yl )-N-ethylbenzenesulfonamide 2-(1-4-(N,N-Diethylsulfamoyl)-phenyl)-4-((2-ethylanilino)-methylene)-4,5-dihydro-5-oxo-1H-pyrazol-3-yl)-ethylacetate 2-(1-4-(N,N-Diethylsulfamoyl)-phenyl)-4-((2-ethoxylanilino)-methylene)-4,5-dihydro-5-oxo-1H-pyrazol-3-yl)-ethylacetate 2-(1-(4-Acetamidophenyl)-4-((2-ethylanilino)-methylene)-4,5-dihydro-5-oxo-1H-pyrazol-3-yl)-ethylacetate 2-(4-((2-Ethylanilino)-methylene)-4,5-dihydro-5-oxo-1-(4-trifluoracetamidophenyl)-1H-pyrazol-3-yl)-ethylacetate 2-(1-(4-Ethoxycarbonylaminophenyl)-4-((2-ethylanilino)-methylene)-4,5-dihydro-5-oxo-1H-pyrazol-3-yl)-ethylacetate 2-(4-((2-Ethylanilinomethylene)-4,5-dihydro-1-(4-methansulfonamidophenyl)-5-oxo-1H-pyrazol-3-yl)-ethylacetate N-(3-(4-(2-Ethylanilinomethylene)-4,5-dihydro-3-methyl-5-oxo-5H-pyrazol-1-yl)-phenyl)-acetamide N,N-Diethyl-4-(4-(2-ethylanilinomethylene)-4,5-dihydro-3-methyl-5-oxo-1H-pyrazol-1-yl)-benzenesulfonamide N-Ethyl-4-(4-(2-ethylanilinomethylene)-4,5-dihydro-3-methyl-5-oxo-1H-pyrazol-1-yl)-benzenesulfonamide 4-(2-Ethoxyanilinomethylene)-2,4-dihydro-5-methyl-2-(4-(4-morpholinylsulfonyl)-phenyl)-3H-pyrazol-3-one 4-(2-Ethylanilinomethylene)-2,4-dihydro-5-methyl-2-(4-(4-methyl-1-piperazinylsulfonyl)-phenyl)-3H-pyrazol-3-one N-(3-(4-(2-Ethylanilinomethylene)-4,5-dihydro-3-methyl-5-oxo-1H-pyrazol-1-yl)-phenyl)-methansulfonamide N-(3-(4-(2-Ethylanilinomethylene)-4,5-dihydro-3-methyl-5-oxo-1H-pyrazol-1-yl)-phenyl)-trifluoroacetamide N-(4-(4-(2-Ethylanilinomethylene)-4,5-dihydro-3-methyl-5-oxo-1H-pyrazol-1-yl)-phenyl)-N-methylsulfonylmethansulfonamide N,N-Diethyl(4,5-dihydro-4-(2-ethoxyanilinomethylene)-3-methyl-5-oxo-1H-pyrazol-1-yl)-benzenesulfonamide N,N-Diethyl-4-(4,5-dihydro-4-(2-methoxyanilinomethylene)-3-methyl-5-oxo-1H-pyrazol-1-yl)-benzenesulfonamide 3-(4-(Ethylanilinomethylene)-4,5-dihydro-5-oxo-3-propyl-1H-pyrazol-1-yl)-benzenesulfonic acid 4-(4-(2-Ethylanilinomethylene)-4,5-dihydro-5-oxo-3-propyl-1H-pyrazol-1-yl)-benzenesulfonic acid 2-(4-(2-Ethylanilinomethylene)-4,5-dihydro-1-(4-nitrophenyl)-5-oxo-1H-pyrazol-3-yl)-ethylacetate 4-(4-(2-Ethylanilinomethylene)-4,5-dihydro-5-oxo-3-propyl-1H-pyrazol-1-yl)-benzoic acid 4-(4-(2-Ethylanilinomethylene)-4,5-dihydro-3-methyl-5-oxo-1H-pyrazol-1-yl)-N-hexylbenzamide 4-(4-(2-Ethylanilinomethylene)-4,5-dihydro-3-methyl-5-oxo-1H-pyrazol-1-yl)-benzamide N,N-Diethyl-4-(4-(2-ethylanilinomethylene)-4,5-dihydro-3-methyl-5-oxo-1H-pyrazol-1-yl)-benzamide 4-(2-Ethylanilinomethylene)-2,4-dihydro-5-propyl-2-(4-pyridyl)-3H-pyrazol-)-one N,N-Diethyl-4-(4-(2-ethylanilinomethylene)-4,5-dihydro-5-oxo-3-propyl-1H-pyrazol-1-yl)-benzamide 4-(4-(2-Ethylanilinomethylene)-4,5-dihydro-5-oxo-3-propyl-1H-pyrazol-1-yl)-N-hexylbenzamide 4-(4-(2-Ethylanilinomethylene)-4,5-dihydro-5-oxo-3-propyl-1H-pyrazol-1-yl)-benzamide 4-(2-Ethylanilinomethylene)-2,4-dihydro-5-propyl-2-(4-(1H-tetrazol-5-yl)-phenyl)-3H-pyrazol-3-one 4-(2-Ethylanilinomethylene)-2,4-dihydro-5-methyl-2-(3-(1H-tetrazol-5-yl)-phenyl)-3H-pyrazol-3-one 4-(4,5-Dihydro-3-methyl-5-oxo-4-(2-trifluoromethylanilinomethylene)-1H-pyrazol-1-yl)-benzoic acid 4-(4-(2-Ethylanilinomethylene)-3-ethoxycarbonylmethyl-4,5-dihydro-5-oxo-1H-pyrazol-1-yl)-benzoic acid 4-(4,5-Dihydro-3-methyl-5-oxo-4-(2-(2-propiyloxy)-anilinomethylene)-1H-pyrazol-1-yl)-benzoic acid 4-(4,5-Dihydro-3-methyl-5-oxo-4-(2-propoxyanilinomethylene)-1H-pyrazol-1-yl)-benzoic acid 4-(4,5-Dihydro4-(2-isopropylanilinomethylene)-3-methyl-5-oxo-1H-pyrazol-1-yl)-benzoic acid 3-(4-(2-Ethylanilinomethyleneaminomethylene)-4,5-dihydro-3-methyl-5-oxo-1H-pyrazol-1-yl)-benzenesulfonamide 2-(1-(4-Methoxycarbonylaminophenyl)-4-((2-ethylanilino)-methylene)-4,5-dihydro-5-oxo-1H-pyrazol-3-yl)-ethylacetate 2-(1-(4-(N,N-Diethylsulfamoyl)-phenyl)-4-(2-ethylanilinomethylene)-4,5-dihydro-5-oxo-1H-pyrazol-3-yl)-ethylacetate 2-(1-(4-(N,N-Diethylsulfamoyl)-phenyl)-4-(2-ethoxyanilinomethylene)-4,5-dihydro-5-oxo-1H-pyrazol-3-yl)-ethylacetate 2-(1-(4-Acetamidophenyl)-4-(2-ethylanilinomethylene)-4,5-dihydro-5-oxo-1H-pyrazol-3-yl)-ethylacetate 2-(4-(2-Ethylanilinomethylene)-4,5-dihydro-5-oxo-1-(4-trifluoroacetamido phenyl)-1H-pyrazol-3-yl)-ethylacetate 2-(4-(2-Ethylanilinomethylene)-4,5-dihydro-1-(4-methoxycarbonylaminophenyl)-5-oxo-1H-pyrazol-3-yl)-ethylacetate 2-(4-(2-Ethylanilinomethylene)-4,5-dihydro-1-(4-methansulfonamidophenyl)-5-oxo-1H-pyrazol-3-yl)-ethylacetate 2-(1-(4-Acetamidophenyl)-4-(2-ethylanilinomethylene)-4,5-dihydro-5-oxo-1H-pyrazol-3-yl)-ethylacetate 2-(4-(2-Ethytanilinomethylene)-4,5-dihydro-5-oxo-1-(4-trifluoroacetamidophenyl)-1H-pyrazol-3-yl)-ethylacetate 2-(4-(2-Ethylanilinomethylene)-4,5-dihydro-1-(4-methoxycarbonylaminophenyl)-5-oxo-1H-pyrazol-3-yl)-ethylacetate 2-(4-(2-Ethylanilinomethylene)-4,5-dihydro-5-oxo-1-(4methanesulfonamidophenyl)-5-oxo-1H-pyrazol-3-yl)-ethylacetate N-(3-(4-(2-Ethylanilinomethylene)-4,5-dihydro-5-oxo-3-propyl-1H-pyrazol-1-yl)-phenyl)-methansulfonamide N-(3-(4-(2-Ethylanilinomethylene))-4,5-dihydro-5-oxo-3-propyl-1H-pyrazol-1-yl)-phenyl)-acetamide N-(3-(4-(2-Ethylanilinomethylene)-4,5-dihydro-5-oxo-3-propyl-1H-pyrazol-1-yl)-phenyl)-carbamic acid methyl-ester 2-(4-(2-Ethylanilinomethylene)-4,5-dihydro-5-oxo-1-(3-trifluoroacetamnido phenyl)-1H-pyrazol-1-yl)-ethylacetate 2-(4-(2-Ethylanilinomethylene)-4,5-dihydro-1-(3-methansulfonamidophenyl)-5-oxo-1H-pyrazol-3-yl)-ethylacetate 4-(4-(2-ethylanilinomethylene)-4,5-dihydro-5-oxo-3-methyl-1H-pyrazol-1-yl)-benzoic acid N-(4-(4-(2-ethylanilinomethylene)-4,5-dihydro-5-oxo-3-methyl-1H-pyrazol-1-yl)-phenyl)-acetamide 2-(4-(2-ethylanilinomethylene)-4,5-dihydro-1-(4-N,N-diethylsulfonamido)-phenyl)-5-oxo-1H-pyrazol-3-yl)-ethyl acetate N-(4-(4-(2-ethylanilinomethylene)-4,5-dihydro-3-methyl-5-oxo-1H-pyrazol-1-yl)-phenyl)-N-methyl-methylsulfonamide 4-[(2-methoxy-phenylamino)methylene]-2,4-dihydro-5-methyl-2-phenyl-pyrazol-3-one 4-[(2-propoxy-phenylamino)methylene]-2,4-dihydro-5-methyl-2-phenyl-pyrazol-3-one 4-(2-ethylanilinomethylene)-2,4-dihydro-5-propyl-2-(4-methoxybenzyl)-pyrazol-3-one 4-(2-ethylanilinomethylene)-2,4-dhydro-5-(2-hydroxyethyl)-2-phenyl-pyrazol-3-one 4-(2-ethylanilinomethylene)-2,4-dihydro-5-propyl-2-(4-bromophenyl)-pyrazol-3-one 4-(2-ethylanilinomethylene)-2,4-dihydro-5-propyl-2-(4-nitrophenyl)-pyrazol-3-one 4-(2-ethylanilinomethylene)-2,4-dihydro-5-methyl-2-(4-nitrophenyl)-pyrazol-3-one 4-(2-ethylanilinomethylene)-2,4-dihydro-5-propyl-2-(2-pyridyl)-pyrazol-3-one 4-(2-ethylanilinomethylene)-2,4-dihydro-5-methyl-2-(2-pyridyl)-pyrazol-3-one 4-(4-(2-Ethylariulinomethylene)-4,5-dihydro-5-oxo-3-methyl-1H-pyrazol-1-yl)-N,N-diethylbenzamide 4-(2-ethylaridlinomethylene)-2,4-dihydro-5-propyl-2-(4-pyridyl)-pyrazol-3-one 4-(2-ethylanilinomethylene)-2,4-dihydro-5-methyl-2-(4-chlorophenyl)-pyrazol-3-one 4-(4-(2-ethylanilinomethylene)-4,5-dihydro-5-oxo-3-propyl-1H-pyrazol-1-yl)-N,N-diethylbenzamide 4-(4-(2-Ethylanilinomethylene)-4,5-dihydro-5-oxo-3-propyl-1H-pyrazol-1-yl)-berizonitfile 3-(4-(2-ethylanilinomethylene)-4,5-dihydro-5-oxo-3-propyl-1H-pyrazol-1-yl)-N-N-diethyl-4-methoxy-benzenesulfonamide 3-(4-(2-ethylanilinomethylene)-4,5-dihydro-5-oxo-3-methyl-1H-pyrazol-l1-yl)-benzonitrile 3-(4-(2-ethylanilinomethylene)-4,5-dihydro-5-oxo-3-methyl-1H-pyrazol-1-yl-methyl)-N-hexyl-4-propoxy-benzenesulfonamnide 3-(4-(2-Ethylanilinomethylene)-4,5-dihydro-5-oxo-3-propyl-1H-pyrazol-1-yl)-benzoic acid N-(3-(4-(2-ethylanilinomethylene)-4,5-dihydro-5-oxo-3-methyl-1H-pyrazol-1-yl)-phenyl)-acetamide 4-(2-ethylanilinomethylene)-2,4-dihydro-5-propyl-2-(4-(1H-tetrazol-5-yl)-phenyl)-pyrazol-3-one 4-(2-ethylanilinomethylene)-2,4-dihydro-5-propyl-2-(3-pyridyl)-pyrazol-3-one 4-(2-ethylanilinomethylene)-2,4-dihydro-5-methyl-2-(3-(1H-tetrazol-5-yl)-phenyl)-pyrazol-3-one 4-(4-(2-ethylanilinomethylene)-4,5-dihydro-5-oxo-3-methyl-1H-pyrazol-1-yl)-N-ethyl-benzene sulfonamide 4-(2-butoxyanilinomethylene)-2,4-dihydro-5-methyl-2-(4-(4-morpholinylsulfonyl)-phenyl-pyrazol-3-one 4-(2-ethoxyanilinomethylene)-2,4-dihydro-5-methyl-2-(4-(4-morpholinylsulfonyl)-phenyl)-pyrazol-3-one 4-(2-ethylanilinomethylene)-2,4-dihydro-5-methyl-2-(4-(4-methyl-1-piperazinylsulfonyl)-phenyl)-pyrazol-3-one N-(3-(4-(2-ethylanilinomethylene)-4,5-dihydro-5-oxo-3-methyl-1H-pyrazol-1-yl)-phenyl)-methansulfonamide N-(3-(4-(2-ethylanilinomethylene)-4,5-dihydro-5-oxo-3-methyl-1H-pyrazol-1-yl)-phenyl)-carbamic acid methyl ester N-(2-(4-(2-ethylanilinomethylene)-4,5-dihydro-5-oxo-3-methyl-1H-pyrazol-1-yl)-phenyl)-methansulfonamide N-(3-(4-(2-ethylanilinomethylene)-4,5-dihydro-5-oxo-3-methyl-1H-pyrazol-1-yl)-phenyl)-triuoroacetamide 4-(4-(2-ethoxyanilinomethylene)-4,5-dihydro-5-oxo-3-methyl-1H-pyrazol-1-yl)-N,N-diethyl-benzenesulfonamide 4-(4-(2-methoxyanilinomethylene)-4,5-dihydro-5-oxo-3-methyl-1H-pyrazol-1-yl)-N,N-diethyl-benzenesulfonamide 4-(4-(2-ethoxyanilinomethylene)-4,5-dihydro-5-oxo-3-methyl-1H-pyrazol-1-yl)-N-ethyl-benzenesulfonamide N-(4-(4-(2-methoxyanilinomethylene)-4,5-dihydro-5-oxo-3-methyl-1H-pyrazol-1-yl-phenyl-carbamic acid ethyl ester 4-(4-(2-trifluoromethylanilinomethylene)-4,5-dihydro-5-oxo-3-methyl-1H-pyrazol-1-yl)-benzoic acid 4-(4-(2-propoxyanilinomethylene)-4,5-dihydro-5-oxo-3-methyl-1H-pyrazol-1-yl)-benzoic acid N-(4-(4-(2-ethoxyanilinomethylene)-4,5-dihydro-5-oxo-3-methyl-1H-pyrazol-1-yl)-propionamide 4-(4-(2-methoxyanilinomethylene)-4,5-dihydro-5-oxo-3-methyl-1H-pyrazol-1-yl)-benzoic acid 4-(4-(2-isopropylanilinomethylene)-4,5-dihydro-5-oxo-3-methyl-1H-pyrazol-1-yl)-benzoic acid 4-(2-ethoxyanilinomethylene)-2,4-dihydro-5-methyl-2-(4-(1-piperidylsulfonyl)-phenyl)-pyrazol-3-one 4-(4-(2-ethoxyanilinomethylene)-4,5-dihydro-5-oxo-3-propyl-1H-pyrazol-1-yl)-N-tert-butyl-benzenesulfonamide 4-(4-(2-ethoxyanilinomethylene)-4,5-dihydro-5-oxo-3-methyl-1H-pyrazol-1-yl)-N-acetyl-benzenesulfonamide 4-(4-(2-ethoxyanilinomethylene)-4,5-dihydro-5-oxo-3-methyl-1H-pyrazol-1-yl)-benzenesulfonamide 2-(1-(4-trifluoroacetamidophenyl)-4-(2-ethylanilinomethylene)-4,5-dihydro-5-oxo-1H-pyrazol-3-yl)-ethylacetate.

as well as their physiologically acceptable salts are useful in the practice of this invention of this invention.

Compounds of Formula I can be made as taught in EP743,304, which is incorporated herein by reference. Those compounds can be made starting with compounds of the general Formula II:

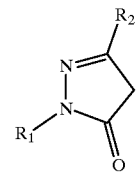

formula II wherein $R_1$ and $R_2$ have designations above. Compounds of Formula II are allowed to react with suitable formaldehyde-donating compounds like triazine or suitable trialkylorthoformates, in particular trirnethylorthoformiate to give compounds of the general formula IIa;

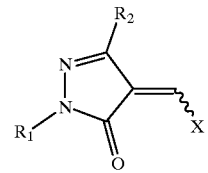

formula IIa wherein X an amino or O-alkyl-group with 1–6 C in the alkyl chain is. These are if necessary, allowed to react in situ with suitable aniline derivatives of Formula III below wherein $R_3$ has the designations above (or salts of Formula III, if necessary) in suitable solvents to give compounds of Formula I and/or one or several substituents $R_{1-3}$ of a compound of Formula I can be transformed to one or several other substituents $R_{1-3}$.

Compounds of Formula II, as well as their starting material reportedly can be synthesized by methods known in the literature or by slightly alterated methods. Suitable methods are described in the patent specification EP-B1-0274 642 or in reference books like Houben Weyl, "Methoden der organischen Chemie", Georg-Thieme-Verlag, Stuttgart, or in literature mentioned in the handbook. "Pyrazolones, Pyrazolidones, and Derivatives", Wiley, R. H., Wiley, P.; Interscience Publishers, John Wiley & Sons (1964) in the following articles: Ringel, C., Mayer, R., J. Prakt. Chem. 26 (1964) 333 ff; Gillespie, J. F.; Price, C. C., J. Org. Chem. 22 (1957) 780 ff;.Tabel, K., Kawvashima, E., Kato, T., Chem. Pharm. Bull (CPBTAL), 29 (1) (1981), 244 ff; Wilson, J. D., Fulmer, T. D., Dasher, L. P., Beam, C. F., J. Heterocycl. Chem. 17 (2) (1980) 389–391); Neunhoefer, H., Koehler, G., Degen H.-J.; Liebigs Ann. Chem.(1985),N 1, 78–89 Ege, S., Adams, A. D., Gess, E. J., Ragone, K. S., Kober, B. J., J. chem. Soc. Perkin Trans. (1983) N 2, 325–321;Pathak, R. B., Bahel, S. C., J. Indian Chem. Soc. 57 (1980) 1108–1111; Ali, M. I., El-Morsy, M. M. S., Hammouda H. A., Sharaf, M. F, Egypt. J. Chem. 22 (1979) 179–188; Mcevoy F. J., Albright J. D., J. org.Chem. 44 (1979) 4597–4603.

In the following reaction steps compounds of Formula II are converted to compounds of Formula I, that can exist as geometrical isomers or isomer mixtures of variable composition. This can take place via an intermediate, where the 4-position of the pyrazoline ring is substituted by a methylenegroup, and the subsequent reaction with an aniline derivative, or it can take place by the direct substitution of a suitable anline derivative.

The choice of the synthetic procedure is herewith influenced by the chemical properties of the substituents of the pyrazolinone.

Some of the synthesized compounds of formula I can exist in a tautomeric equilibrium:

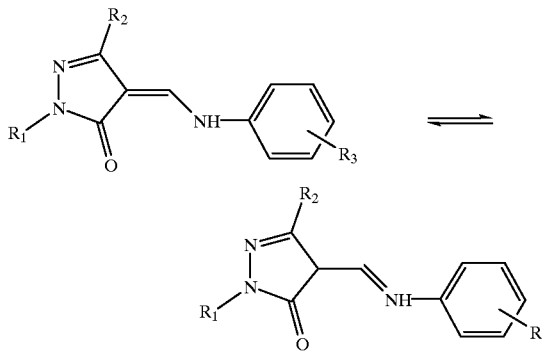

The use of compounds of formula I is always mentioned, although the pure compounds as well as their mixtures with variable portions of the tautomeric resp. (isomeric) compounds are meant.

formula IIa

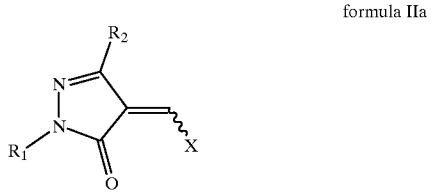

In particular, the new as well as the already known compounds of formula I can be synthesized by the reaction of compounds of the general formula IIa, wherein, $R_1$ and $R_2$ have the above mentioned designation and X is an amino or an alkoxygroup, with a suitable aniline derivative of Formula III, wherein $R_3$ has the above designation.

formula III

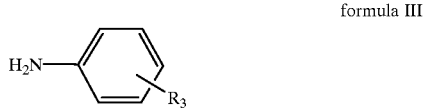

This reaction takes place if necessary, in the presence of a suitable diluent at temperatures from 0°C. to 120° C., especially at elevated temperatures. Compounds of Formula II can be synthesized by the reaction of suitable compounds of the general Formula II with formaldehyde-donating groups selected from the group of triazine, dimethylformamide, dimethylforrnamidedimethylacetal, Gold's Reagent, formic acid chloride, formamide, alkyl-derivatives form amide wvith 1–6 carbons in the alkyl chain or from the group of trialkylorthoformiates, in particular trimethylorthoformide.

If necessary, the reaction takes place in a diluent, e.g. glacial acetic acid, that does not disturb in the use later on, and maybe a suitable catalyst. The compounds of formula IIa can be isolated as intermediates.

Another procedure for the synthesis of compounds of Formula I is preferred if compounds of formula II have sensitive substituents that react preferred with formaldehyde donating compounds or wvith aniline derivatives. In these cases, preferably, a suitable aryl-isocyanate is allowed to react with the respective compound of formula II in the presence of a base, especially butyl-or methyl-lithium.

Compounds of the general formula II are usually synthesized by the reaction of β-ketoesters or 1,3-dicarbonyl compounds of the general formula IV,

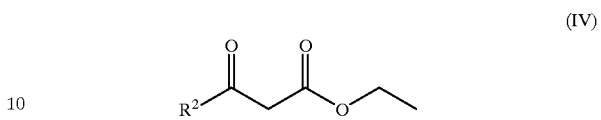

Wherein $R_2$ can have the above mentioned designation, and hydrazines of the general formula V

or their salts like e.g., their hydrochlorides, hydrosulfates, hydrooxalates and others, if necessary in the presence of a suitable diluent, that doesn't disturb in the further use of the reaction product, like e.g., ethanol, and if necessary, in the presence of a catalyst like toluenesulfonic acid, at temperatures between 0° and 120° C.

The employed 1,3-dicarbonyl compounds of Formula IV are generally knowvn compounds of organic chemistry and are either commercially available or they can be synthesized by methods generally known to someone versed in the art. The hydrazines for the cyclization reaction are known compounds and can be synthesized by one skilled in the art by generally known methods (see e.g., Houben Weyl, Methoden der organischen Chemie, Vol. 2, p. 203, Thieme Verlag Stuttgart, 1967).

The compounds of formula I of this invention are preferably administered in dosages between 1 mg and 1 g, especially between 50 and 500 mg. The daily dosage is preferably betveen 0.1 and 50 mg/kg especially between 1 and 10 mg/kg body weight. The special dosage for the individual patient depends on different factors, for example, the activity of the particular compound, the age, body weight, general health, gender, nutrition, administration time and passage, the elimination velocity, pharmaceutical combination and the gravity of the disease, for which the therapy is meant. The oral application is preferred.

In the following, examples from the aforesaid EP patent application illustrate those useful in the practice of this invention; but the invention is not limited to the use of compounds of these examples. In the followving examples the "usual workup" means: water is added, if necessary, the pH is adjusted, if necessary, depending on the constitution of the product to value betveen 2 and 10; extraction is done wvith ethylacetate or dichloromethane, the phases are separated, the organic phase is dried with sodiumsulfate, evaporated and purified by chromatography on silicagel and/or crystallisation.

In the preceding and the following, all temperatures are in ° C.

EXAMPLES

1(a) 5-Methyl-2-(4nitrophenyl)-2,4-dihydro-pyrazol-3-one (Cyclisation reaction) p-Nitrophenylhydrazine-hydrochloride (1.63 g) ethylacetoacetate (1.26) are heated in ethanol (30 ml) for 45 minutes under reflux. The mixture is concentrated in vacuo and the precipitating crystals are collected.

Yield: 1.20 g 5-Methyl-2-(4-nitrophenyl)-2,4-dihydro-pyrazol-3-one (64%) M.p. 223° C.

1(b) 4-(2-Ethylphenylarnmomethylene)-5-methyl-2-(4-nitrophenyl)-2,4-dihydro-pyrazol-3-one (one-step reaction formamide and anilin addition)

5-Methyl-2-(4nitrophenyl)-2,4-dihydro-pyrazol-3-one 1 g, 1,3,5-triazin (190 mg)and 2-ethylanillihne 0.74 ml are refluxed in ethanol (50 ml) 4 days. The solvent is evaporated in vacuo, and the crude product is purified by chromatography on silicagel ($CH_2Cl_2$/MeOH: 97/3).

Yield: 1.33 g 4-(2-ethylphenylaminomethylen)-5-methyl-2-(4-nitrophenyl)-2,4-dihydro-pyrazol-3-one (83%); Mp. 220° C.

1(c) 3-Methyl-4-aminomethylene-1-phenyl-4,5-dihydro-pyrazol-5-one (formamide addition)

To a suspension of 3-methyl-1-phenyl-2-pyrazolin-5-one (52.3 g; 0.3 mol) in ethanol (800 ml) 1,3,4-triazin (8.11 g, 0.1 mol) is added, and the mixture is refluxed for 1 hour. The solution is concentrated, the precipitating crystals are collected in the cold. The crude crystal mixture (24.4 g) is purified by chromatography on silicagel ($CH_2O_2$/Aceton: 4/1) to give the title compound 3-methyl-4-aminomethylene-1-phenyl-4,5-dihydro-pyrazol-5-one.

The mother liquor is concentrated to leave a solid (36 g) which can be purified by the same chromatography as above to give the dimere compound (14.1 g; mp=180.6° C.), which is re-crystallized in acetone.

1(d) 3-Methyl-4-(2-propoxyphenylaminomethylene)-1-phenyl-4,5-dihydro-pyrazol-5-one (aniline addition)

3-methyl-4arninomethylene-1-phenyl-4,5-dihydro-pyrazol-5-one (2 g) and 2-propoxyanilino-trifluoroacetic acid salt (1.6 g) are refluxed 1.5 hours in ethanol.

The reaction mixture is concentrated and purified by chromatography (methylbutylketone/hexane: 4/1), and re-crystallized in methylbutylketone/hexane. Yield: 1.5 g 3-methyl-4-(2-propaxyphenylaminomethylene)-1-phenyl-4,5-dihydro-pyrazol-5-one (45.5%)

No dimer product is to be detected.

1(e) 4-(2-Methoxyphenylaminomethylene)-5-methyl-2-phenyl-2,4-dihydro-pyrazol-3-one 5-Methyl-2-phenyl-2,4-dihydro-pyrazol-3-one 2 g trimethylorthoformiate (188 ml) and o-anisidin (1.29 ml) are heated swith glacial acetic acid (5 ml) to 70° C. for 2 hours. After the reaction mixture cools down, methanol is added. The precipitate is collected and recrystallized in ethylacetate.

Yield: 1.1 g 4-(2-methoxyphenylaminomethylene)-5-methyl-2-phenyl-2,4-dihydro-pyrazol-3-one (31%) Mp. 143° C.

2(a) 4-(4,5-Dihydro-4-(2-ethylanilinomethylene)3-methyl-5-oxo-1H-pyrazol-1-yl)-N-hexyl-benzamide (subsequent derivatisation of the 1-substituent).

4-(4,5-dihydro-4-(2-ethylanilinomethylene)-3-methyl-5-oxo-1H-pyrazol-1-yl)-benzoic acid (0.5 g; 1.43 mol) and hexylamine (0.19 ml; 1.43 mmol) and DMF (20 ml) are stirred at room temperature for 5 minutes. N-(3-dimethylaminopropyl)-N-ethylcarbodiimide HCl(0.27 g; 1.43 mmol) 1-hydroxy-benzotriazole (0.19 g; 1.43 mmol) and N-methylmorpholine (0.18 ml; 1.43 mmol) are added gradually, and the mixture is stirred 3 hours.

The end of the reaction is acertained by thin layer chromatography (TLC in $CH_2Cl_2$/MeOH: 9/1 (tin hydrine spray reagent)).

The reaction mixture is poured into water (200 ml) is extracted with ethyl ether twice; the combined ether layers are dried wvith sodium sulfate are filtrated and the ether is evaporated in vacuo. The residue is purified by chromatography or silicagel $Si_6O$ (methylbutylether)

Yield: 250 mg 4-(4,5-dihydro-4-(2-ethylanilinomethylene)-3-methyl-5-oxo-1H-pyrazol-1-yl)-N-hexyl-benzarnide (41.6%)

2(b) 4-(2-Ethylanilinomethylene)-4,5-dihydro-3-methyl-1-(3-(1H-tetrazol-5-yl)-phenyl)-1H-pyrazol-5-one (subsequent derivatisation of the 1-substituent)

3-(4,5-dihydro-4-(2-ethylanilinomethylene)-3-methyl-5-oxo-1H-pyrazol-1-yl) benzonitrile (200 mg; 0.6 mmol) trimethyltinazide (480 mg; 2.4 mmol) and toluane (20 ml) are mixed and refluxed for 2 days. Small amounts of starting material are still detectable by TLC. The workup is the following:

The precipitate is collected. It is the product that is contaminated only by Sn-salts. The product is therefore purified by chromotography over silicagel $Si_6O$ ($CH_2Cl_2$/MeOH: 9/1)

Yield 100 mg 4-(2-ethylanillnomethylene)-4,5-dihydro-3-methyl-1-(3-(1H-tetrazol-5-yl)-phenyl-1H-pyrazol-5-one (45.5%).

Besides the compounds of Examples 1 and 2, the following pyrazol-3-one-derivatives of Formula 1 can be made by the described method with triazine or trimethyl formate:

3. From 4-(4-morphollnyl)sulfonylphenylhydrazin and ethylacetacetate: 5-methyl-2-(4-(-4-morpholinyl)-sulfonylphenyl)-2, 4-dihydro-pyrazol-3-one and 2-ethylaniline 4-(2-ethylanilinomethylene)-2,4-dihydro-5-methyl-2-(4-(4-morpholinyl)-sulfonylphenyl)-3H-pyrazol-3-one Mp. 275° C.

4. From phenylhydrazine-3-acetamide and ethylacetoacetate: N-(3-(-4,5-dihydro-3-methyl-5-oxo-5H-pyrazol-1-yl) phenyl)-acetamide and 2-ethylaniline N-(3-(4-(2-ethylanilinomethylene)-4,5-dihydro-3-methyl-5-oxo-5H-pyrazol-1-yl)-acetamide Mp: 253° C.

5. From N,N-diethyl-4-hydrazinobenzenesulfonamide and ethylacetacetate: N,N-diethyl-4-(4,5-dihydro-3-methyl-5-oxo-1H-pyrazol-1-yl)-benzenesulfonamnide and 2-ethylaniline N,N-diethyl-4-(4-(2-ethylanilinomethylene)-4,5-dihydro-3-methyl-5-oxo-1H-pyrazol-1-yl) benzenesulfonamide, Mp: 194° C.

6. From N-ethyl-4-hydrazinobenzenesulfonamide and ethylacetoacetate: N-ethyl-4-(4,5-dihydro-3-methyl-5-oxo-1H-pyrazol-1-yl)-benzenesulfonamide and 2-ethylaniline N-ethyl-4-(4-(2-ethylanilinine)-4,5-dihydro-3-methyl-5-oxo-1H-pyrazol-1-yl)benzenesulfonamide Mp: 260° C.

7. From 4-(4-Morpholinyl)-sulfonylphenylhydrazine and ethylacetate: 5-methyl-2-(4-(4-morpholinyl)-sulfonylphenyl)-2,4-dihydro-pyrazol-3-one and 2-butoxyaniline 4-(2-butoxyanilinomethylene)-2,4-dihydro-5-methyl-2-(4-(4morphohnylsulfonyl)-phenyl)-3H-pyrazol-3-one, Mp: 171° C.

8. From 4-(4morpholinyl)sulfonylphenylthydrazine and ethylacetacete: 5-methyl-2-(4-(4morpholinyl)-sulfonylphenyl)-2,4-dihydro-pyrazol-3-one and 2-ethoxyaniline 4-(2-ethoxyanlinomethylene)-2, 4-dihydro-5-methyl-2-(4-(4morpholinylsulfonyl)-phenyl)-3H-pyrazol-3-one Mp: 265° C.

9. From 4-(4-methylpiperazinyl)-sulfonylphenylhydrazine and ethylacetace: 5-methyl-2-(4-(4-methylpiperazinyl)-sulfonylphenyl)-2,4-dihydro-pyrazol-3-one and 2-ethylaniline 4-(2-ethylanilinomethylene)-2,4-dihydro-5-methyl-2-(4-(4-methyl-1-piperazinylsulfonyl)-phenyl)-3H-pyrazol-3-one Mp: 254° C.

10a. 2-(3-Aminophenyl)-5-methyl-2,4-dihydropyrazol-2-one (hydration of a substituent)

A solution of 5-methyl-2-(3-nitrophenyl)-2,4-dihydro-pyrazol-3-one (15 g) in methanol (400 ml) is hydrated in the presence of Raney-Nickel (10 g). The catalyst is filtered off, and the solution is concentrated in vacuo Yields 2-(3-Aminophenyl)-5-methyl-2,4-dihydropyrazol-2-one. The following compounds can be made in a similar fashion 2-(4-Aminophenyl)-5-methyl-2,4-dihydopyrazol-2-one 2-(2-Aminophenyl)-5-methyl-2,4-dihydropyrazol-2-one A solution of 2-(3-aminophenyl)-5-methyl-2,4-dihydro-pyrazol-3-one (4.0 g) in dichloromethane (30 ml) and pyridine (2 ml) is charged under ice cooling with methanesulfonylchloride (2.2 ml) and is stirred for 2 hours. The solution is washed with diluted HCl and water, is dried and concentrated in vacuo. The obtained N-(3-(4,5-dihydro-3-methyl-5-oxo-1H-pyrazol-1-yl)-phenyl)-methanesulfonamide and 2-ethylaniline react to N-(3-(4-2-ethylanilinomethylene)-4,5-dihydro-3-methyl-5-oxo-1H-pyrazol-1-yl)-phenyl-methanesulfonamide Mp. 192° C.

11. Reaction of the amino group of the N-substituents of pyrazole with methylchloroformiate or sulfonic acid chloride.

A solution of 2-(3-aminophenyl)-5-methyl-2,4-dihydro-pyrazol-3-one (4.0 g) in dichloromethane and pyridine (2 ml) is charged under ice cooling with methylchloroformiate (2.2 ml) and is stirred for 2 hours. The solution is washed with diluted HCl and water, is dried and concentrated in vacuo.

Yield: 4.2 g N-(3-(4,5-dihydro-3-methyl-5-oxo-1H-pyrazol-1-yl)-phenyl-carbamic acid methylester (65%) oil. Further reaction with 2-ethylaniline gives N-(3-(4-(2-ethylanilinomethylen)-4,5-dihydro-3-methyl-5-oxo-1H-pyrazol-1-yl)-phenyl-carbamic acid methylester Mp. 229° C.

Similarly, from 2-(4-aminophenyl)-5-methyl-2,4-dihydro-pyrazol-3-one and methanesulfonic acid chloride is obtained N-(4-(4,5-dihydro-3-methyl-5-oxo-1H-pyrazol-1-yl)-phenyl-methanesulfonamide and from 2-(4-aminophenyl)-5-methyl-2,4-dihydro-pyrazol-3-one methyl chlorofomate is obtained N-(4-(4,5-dihydro-3-methyl-5-oxo-1H-pyrazol-1-yl)-phenyl-carbamlic acid methylester.

12. N-(4-Phenyl-(4,5-dihydro-3-methyl-5-oxo-1H-pyrazol-1-yl-acetamide (The reaction of amino group of the N-substituent of the pyrazol with acetic acid derivatives)

2-(4-Aminophenyl)-5-methyl-2,4-dihydro-pyrazol-3-one (1.9 g) in tetrahydrofliran (40 ml) is charged wvith acetic anhydride (1.0 ml), and the mixture is stirred for 2 hours. The solution is concentrated in vacuo, and the residue is worked up as usual.

Yield: 1.5 g N-(4-phenyl-(4,5-dihydro-3-methyl-5-oxo-1H-pryazol-1-yl)-acetamide (65%)

Similarly, from the reaction of 2-(4-aminophenyl)-5-methyl-2,4-dihydro-pyrazol-3-one and trifluoroacetic anhydride is obtained N-(4-phenyl-(4,5-dihydro-3-methyl-5-oxo-1H-pyrazol-1-yl)-trifluoroacetamnide Similarly, from the reaction of 2-(3-aminophenyl)-5-methyl-2,4-dihydro-pyrazol-3-one and trifluoroacetic anhydride is obtained N-(3-phenyl-(4,5-dihydro-3-methyl-5-oxo-1H-pyrazol-1-yl)-trifluoroacetamide.

Simllarly, from the reaction of 2-(3-aminophenyl)-5-methyl-2,4-dihydro-pyrazol-3-one and acetic anhydride is obtained N-(3-phenyl-(4,5-dihydro-3-methyl-5-oxo-1H-pyrazol-1-yl)-acetamide Similarly, from the reaction of 5-methyl-2-(4-aminophenyl)-2,4-dihydro-pyrazol-3-one (synthesized as in Example 10) and acetic anhydride is obtained N-(4-phenyl (4,5-dihydro-3-methyl-5-oxo-5H-pyrazol-1-yl))-acetamide. By reaction of N-(4-phenyl(-4,5-dihydro-3-methyl-5-oxo-5H-pyrazol-1-yl))-acetamide with 2-ethylaniline, N-(4-(4-(2-ethylanilinomethylene)-4,5-dihydro-3-methyl-5-oxo-1H-pyrazol-1-yl)-phenyl)-acetamide is obtained Mp: 230° C.

13. From the reaction of 5-methyl-2-(4-aminophenyl)-2,4-dihydro-pyrazol-3-one and methansulfonylchloride (reaction per Example 11, where methanesulfonylchloride is used in respective molecular amounts), N-(4-(4,5-dihydro-3-methyl-5-oxo-1H-pyrazol-1-yl)-phenyl)-N-methylsulfonylmethanesulfonamide is obtained. Subsequent reaction with 2-ethyl aniline yields N-(4-(4-(2-Ethylanilinomethylene)-4,5-dihydro-3-methyl-5-oxo-1H-pyrazol-1-yl)-phenyl)-N-methylsulfonylmethansulfonamide, Mp: 268° C.

14. From the reaction of 5-Methyl-2-(2-anminophenyl)-2,4-dihydro-pyrazol-3-one and methanesulfonylchloride (reaction like Example 11), N-(4-(4,5-dihydro-3-methyl-5-oxo-1H-pyrazol-1-yl)-phenyl)-methanesulfonamide is obtained. Subsequent reaction with 2-ethylaniline yields N-(2-(4-(2-ethylanilinomethylene)-4,5-dihydro-3-methyl-5-oxo-1H-pyrazol-1-yl)-phenyl)-methanesulfonamide Mp. :231° C.

15. From the reaction of 5-methyl-2-(3-aminophenyl)-2,4-dihydro-pyrazol-3-one and trifluoroacetic anhydride (reaction like Example 12) is obtained N-(3-phenyl(-4,5-dihydro-3-methyl-5-oxo-1H-pyrazol-5-yl))-trifluoroacetamide. Subsequent reaction with 2-ethylaniline yields N-(3-(4-(2-ethylanilinomethylene)-4,5-dihydro-3-methyl-5-oxo-1H-pyrazol- 5-yl)-phenyl)-trifluoroacetamide, Mp: 240° C.

16. From the reaction of N,N-diethyl-4-hydrazinobenzenesulfonamide and ethylacetoacetate gives N,N diethyl-4-(4,5-dihydro-3-methyl-5-oxo-1H-pyrazol-1-yl)-benzenesulfonamide. Subsequent reaction wvith 2-ethoxyaniline yields N,N-diethyl4-(4,5-dihydro-4-(2-ethoxyanilinomethylene)-3-methyl-5-oxo-1H-pyrazol-1-yl)-benzenesulfonamide, Mp: 170° C.

17. From the reaction of N,N-diethyl-4-hydrazinobenzenesulfonamide and ethylacetoacetate: yields N,N-diethyl-4-(4,5-dihydro-3-methyl-5-oxo-1H-pyrazol-1-yl)-benzenesulfonamide. Subsequent reaction with 2-methoxyaniline yields N,N-diethyl-4-(4,5-dihydro-4-(2-methoxyanilinomethylene)-3-methyl-5-oxo-1H-pyrazol-1-yl)-benzenesulfonamide, Mp: 191° C.

18. From the reaction of N-ethyl-4-hydrazinobenzolsulfonamide and ethylacetoacetate yields N-ethyl-4-(4,5-dihydro-3-methyl-5-oxo-1H-pyrazol-1-yl)-benzenesulfonamide. Subsequent reaction with 2-ethoxyaniline yields 4-((2-ethoxyanilinomethylene)-4,5-dihydro-3-methyl-5-oxo-1H-pyrazol-1-yl)-N-ethylbenzenesulfonamide, Mp: 238° C.

19. From the reaction of 5-methyl-2-(4-aminophenyl)-2,4-dihydro-pyrazol-3-one and ethylchloroformate (per the reaction in Example 11) yields N-(4-(4,5-dihydro-3-methyl-5-oxo-1H-pyrazol-1-yl)-phenyl-carbamic acid ethyl ester. Subsequent reaction with 2-methoxyaniline yields N-(4-(4,5-dihydro-4-(2-methoxyanilinomethylene)-3-methyl-5-oxo-1H-pyrazol-1-yl)-phenyl)-carbamic acid ethyl ester, Mp: 212° C.

20. From the reaction of 5-methyl-2-(4-aminophenyl)-2,4-dihydro-pyrazol-3-one and propionylchloride (per the procedure of Example 11), N-(4-(4,5-dihydro-3-methyl-5-oxo-1H-pyrazol-1-yl)-phenyl) propionamide is obtained. The subsequent reaction with-2-ethoxyaniline yields N-(4-(4-(2-Ethoxyanilinomethylene)-4,5-dihydro-3-methyl-5-oxo-(1H-pyrazol-1-yl)-phenyl)-propionamide, Mp: 208° C.

21. From the reaction of 4-(1-piperidyl)-sulfonylphenylhydrazine and ethylacetoacetate, 5-methyl-2-(4-(1-piperidylsulfonyl)-phenyl)-3H-pyrazol-3-one is obtained. Subsequent reaction with 2-ethoxyaniline yields 4-(2-ethoxyanilinomethylene)-2,4-dihydro-5-methyl-2-(4-(1-piperidylsulfonyl)-phenyl)-3H-pyrazol-3-one, Mp: 252° C.

22. From the reaction of N-tert.-butyl-4-hydrazinobenzenesulfonamide and ethylbutyrylacetate, N-tert.-Butyl-4-(4,5-dihydro-3-propyl-5-oxo-1H-pyrazol-1-yl)-benzenesulfonamide is obtained. Subsequent reaction with 2-ethoxyaniline yields N-tert-butyl-4-(4-(2-ethoxyanilinomethylen)-4,5-dihydro-3-propyl-5-oxo-1H-pyrazol-1-yl)-benzenesulfonamide, Mp: 254° C.

23. N-Acetyl-4-(4-(2-Ethoxyanilinomethylene)-4,5-dihydro-3-methyl-5-oxo-1H-pyrazol-1-yl)-benzenesulfonamide (derivatisation of the N-substituent of the pyrazols after condensation of the aniline derivative).

To a solution of 4-(4-(2-ethoxyanilinomethylene)-4,5-dihydro-3-methyl-5-oxo-1H-pyrazol-1-yl) benzenesulfonamide (1.0 g) and dimethylamninopyridin (0.9 g) in pyridine (30 ml) is dropped under ice cooling and the mixture is stirred for 10 hours. The mixture is concentrated and the residue is charged with dil HCl. The praecipitated crystals are collected and are ground with ethanol.

Yield 0.47 g N-Acetyl-4-(4-2-ethoxyanilinomethylene)-4,5-dihydro-3-methyl-5-oxo-(1H-pyrazol-1-yl)-benzenesulfonamide (42.5%): Mp.: 282° C.

24. From the reaction of 4-hydrazinobenzenesulfonamide and ethylacetoacetate, 4-(4,5-dihydro-3-methyl-5-oxo-1H-pyrazo-1-yl)-benzenesulfonamide is obtained. Subsequent reaction with 2-ethoxyaniline yields 4-(4-(2-Ethoxyanilinomethylene)-4,5-dihydro-3-methyl-5-oxo-1H-pyrazol-1-yl)-benzenesulfonamide,
Mp.: 241° C.

25. From the reaction of phenylhydrazine and 5-hydroxy-3-oxo-pentanoic acid methyl ester 5-(2-hydroxyethyl)-2-phenyl-2,4-dihydropyrazol-3-one is obtained. Subsequent reaction with 2-ethylaniline yields 4-(2-ethylanilinomethylene)-2,4-dihydro-5-(2-hydroxyethyl)-2-phenyl-1H-pyrazol-3-one 26. From the reaction of 4-methoxybenzylhydrazine and ethylbutyrylacetate, 2,4-dihydro-2-(4-methoxybenzyl)-5-propyl-3H-pyrazol-3-one is obtained. Subsequent reaction with 2-ethylaniline yields 4-(2-ethylanilinomethylene)-2,4-dihydro-2-(4-methoxybenzyl)-5-propyl-3H-pyrazol-3-one, oil 27. From the reaction of 2-propoxybenzylhydrazine and ethylbutyiylacetate, 2,4-Dihydro-2-(2-propoxybenzyl)-5-propyl-3H-pyrazol-3-one is obtained. Subsequent reaction with 2-ethylaniline yields 4-(2-ethylanilinomethylene)-2,4-dihydro-2-(2-propoxybenzyl)-5-propyl-3H-pyrazol-3-one, Mp. 75.2° C.

28. From the reaction of 4-bromophenylhydrazine and ethylbutyrylacetate, 2-(4-bromphenyl)-2,4-dihydro-5-propyl-3H-pyrazol-3-one is obtained. Subsequent reaction with 2-ethylaniline yields 2-(4-bromophenyl)-4-(2-ethylanilinomethylene)-2,4-dihydro-5-propyl-3H-pyrazol-3-one, Mp.: 126.9° C.

29. From the reaction of 4-nitrophenylhydrazine and ethylbutyrylacetate, 2,4-dihydro-2-(4-nitrophenyl)-5-propyl-3H-pyrazol-3-one is obtained. Subsequent reaction with 2-ethylaniline yields 4-(2-ethylanilinomethylene)-2,4-dihydro-2-(4-nitrophenyl)-5-propyl-3H-pyrazol-3-one, Mp 211° C.

30. From the reaction of 3-hydrazinobenzenesulfonic acid and ethylbutyrylacetate, 3-(4,5-Dihydro-5-oxo-3-propyl-1H-pyrazol-1-yl)-benzenesulfonic acid is obtained. Subsequent reaction with 2-ethylaniline yields 3-(4-(2-ethylanilinomethylene)-4,5-dihydro-5-oxo-3-propyl-1H-pyrazol-1-y 1)-benzenesulfonic acid, Mp 258.6° C.

31. From the reaction of 4hydrazinobenzenesulfonic acid and ethylbuturylacetate, 4-(4,5-dihydro-5-oxo-3-propyl-1H-pyrazol-1-yl)-benzenesulfonic acid is obtained. Subsequent reaction with 2-ethylaniline yields 4-(4-(2-ethylanilinomethylene)-4,5-dihydro-5-oxo-3-propyl-1H-pyrazol-1-yl)-benzenesulfonic acid Mp: 205° C.

32. From the reaction of 4-nitrophenylhydrazine and diethyl-3-oxoglutarate, 2-(4,5-dihydro-1-(4-nitrophenyl)-5-oxo-1H-pyrazol-3-yl)-ethylacetate is obtained. Subsequent reaction with 2-ethylaniline yields 2-(4-(2-ethylanilinomethylene)-4,5-dihydro-1-(4-nitrophenyl)-5-oxo-1H-pyrazol-3-yl)-ethylacetate Mp 224.5° C.

33. From the reaction of 4-hydrazinobenzoic acid and ethylacetoacetate, 4-(4,5-dihydro-5-oxo-3-methyl-1H-pyrazol-1-yl)-benzoic acid is obtained. Subsequent reaction with 2-ethylaniline yeilds 4-(4-(2-ethylanilinomethylene)-4,5-dihydro-5-oxo-3-methyl-1H-pyrazol-1-yl)-benzoic acid, Mp 291° C.

34. From the reaction of 2-pyridylhydrazine and ethylbutyrylacetate, 2,4-dihydro-2-(2-pyridyl)-5-propyl-3H-pyrazol-3-one is obtained. Subsequent reaction with 2-ethylaniline yields 4-(2-ethylanilinomethylene)-2,4-dihydro-2-(2-pyridyl)-5-propyl-3H-pyrazol-3-one, Mp 151° C.

35. From the reaction of 2-pyridylhydrazine and ethylacetoacetate, 2,4-dihydro-5-methyl-2-(2-pyridyl)-3H-pyrazol-3-one is obtained. Subsequent reaction with 2-ethylaniline yields 4-(2-ethylanilinomethylene)-2,4-dihydro-5-methyl-2-(2-pyridyl)-3H-pyrazol-3-one, Mp 182.9° C.

36. From the reaction of 4-hydrazinobenzoic acid and ethylbutyrylacetate, 4-(4,5-dihydro-5-oxo-3-propyl-1H-pyrazol-1-yl)-benzoic acid is obtained. Subsequent reaction with 2-ethylaniline yields 4-(4-(2-ethylanilinomethylene)-4,5-dihydro-5-oxo-3-propyl-1H-pyrazol-1-yl)-benzoic acid, Mp 254.5° C.

37. From the reaction of 4-(4-(2-ethylanilinomethylene)-4,5-dihydro-3-methyl-5-oxo-1H-pyrazol-1-yl)-benzoic acid and hexylamine, 4-(4-(2-ethylanilinomethylene)-4,5-dihydro-3-methyl-5-oxo-1H-pyrazol-1-yl)-N-hexylbenzamide is obtained, Mp 62.1° C.

38. From the reaction of 4-(4-(2-ethylanilinomethylene)-4,5-dihydro-3-methyl-5-oxo-1H-pyrazol-1-yl)-benzoic acid and diluted ammonia solution, 4-(4-(2-ethylanilinomethylene)-4,5-dihydro-3-methyl-5-oxo-1H-pyrazol-1-yl)-benzamide is obtained, Mp 225.2° C.

39. From the reaction of 4-(4-(2-ethylanilinomethylene)-4,5-dihydro-3-methyl-5-oxo-1H-pyrazol-1-yl)-benzoic acid and diluted, N,N-diethylamine solution, N,N-diethyl-4-(4-(2-ethylanilinomethylene)-4,5-dihydro-3-methyl-5-oxo-1H-pyrazol-1-yl)-benzamide is obtained, Mp 112° C.

40. From the reaction of 4-pyridylhydrazine and ethylbutyrylacetate, 2,4-dihydro-5-propyl-2-(4-pyridyl)-3H-pyrazol-3-one is obtained. Subsequent reaction wvith 2-ethylaniline yields 4-(2-ethyianilinomethylene)-2,4-dihydro-5-propyl-2-(4-pyridyl)-3H-pyrazol-3-one, Mp 159.2° C.

41. From the reaction of 4-chlorphenylhydrazine and ethylacetoacetate, 2-(4-chlorphenyl)-2,4-dihydro-5-methyl-3H-pyrazol-3-one is obtained. Subsequent reaction with 2-ethylaniline yields 2-(4chlorphenyl)-4-(2-ethylanilinomethylene)-2,4-dihydro-5-methyl-3H-pyrazol-3-one 42. From the reaction of 4-(4-(2-ethylanilinomethylene)-4,5-dihydro-5-oxo-3-propyl-1H-pyrazol-1-yl)-benzoic acid and diluted diethylamine solution, N,N-diethyl-4-(4-(2-ethylanilinomethylene)-4,5-dihydro-5-oxo-3-propyl-1H-pyrazol-1-yl)-benzamide is obtained, Mp 123° C.

43. From the reaction of 4-(4-(2-ethylanilinomethylene)-4,5-dihydro-5-oxo-3-propyl-1H-pyrazol-1-yl)-benzoic acid and hexylamine, 4-(4-(2-ethylanilinomethylene)-4,5-dihydro-5-oxo-3-propyl-1H-pyrazol-1-yl)-N-hexylbenzamide is obtained, Mp 46.7° C.

44. From the reaction of 4-(4-(2-ethylanilinomethylene)-4,5-dihydro-5-oxo-3-propyl-1H-pyrazol-1-yl)-benzoic acid and diluted ammonia solution, 4-(4-(2-ethylanilinomethylene)-4,5-dihydro-5-oxo-3-propyl-1H-pyrazol-1-yl)-benzamide is obtained, Mp 170° C.

45. From the reaction of 4-hydrazinobenzonitril and ethylbutyrylacetate, 4-(4,5-dihydro-5-oxo-3-propyl-1H-pyrazol-1-yl)-benzonitrile is obtained. Subsequent reaction with 2-ethylaniline yields 4-(4-(2-ethylanilinomethylene)-4,5-dihydro-5-oxo-3-propyl-1H-pyrazol-1-yl)-benzonitrile, Mp 196.7° C.

46. From the reaction of N,N-diethyl-3-hydrazino-4-methoxybenzenesulfonamide and ethylbutyrylacetate, N,N-diethyl-3-(4,5-dihydro-5-oxo-3-propyl-1H-pyrazol-1-yl)-4-methoxybenzenesulfonamide is obtained. Subsequent reaction with 2-ethylaniline yields N,N-diethyl-3-(4-(2-ethylanilinomethylene)-4,5-dihydro-5-oxo-3-propyl-1H-pyrazol-1-yl)-4-methoxybenzenesulfonamide, oil 47. From the reaction of 3-hydrazinobenzonitrile and ethylacetoacetate, 3-(4,5-dihydro-3-methyl-5-oxo-1H-pyrazol-1-yl)-benzonitrile is obtained. Subsequent reaction with 2-ethylaniline yields 3-(4-(2-ethylanilinomethylene)-4,5-dihydro-3-methyl-5-oxo-1H-pyrazol-1-yl)-benzonitrile, Mp 210.8° C.

48. From the reaction of N-hexyl-3-hydrazino-4-propoxybenzolsulfonamide and ethylacetoacetate, 3-(4,5-dihydro-3-methyl-5-oxo-1H-pyrazol-1-ylmethyl)-N-hexyl-4-propoxybenzenesulfonamide is obtained. Subsequent reaction with 2-ethylaniline yields 3-(4-(2-ethylanilinomethylene)-4,5-dihydro-3-methyl-5-oxo-1H-pyrazol-1-ylmethyl)-N-hexyl-4-propoxybenzenesulfonamide, resin 49. From the reaction of 2-hydrazinobenzoic acid and ethylbutyrylacetate, 2-(4,5-dihydro- 5-oxo-3-propyl-1H-pyrazol-1-yl)-benzoic acid is obtained. Subsequent reaction with 2-ethylaniline yields 2-(4-(2-ethylanilinomethylene)-4,5-dihydro-5-oxo-3-propyl-1H-pyrazol-1-yl)-benzoic acid, Mp 126.9° C.

50. From the reaction of 4-(4-(2-ethylaniuomethylene)-4,5-dihydro-5-oxo-3-propyl-1H-pyrazol-1-yl)-benzonitrile and trimethyltinazide 4-(2-ethylanilinomethylene)-2,4-dihydro-5-propyl-2-(4-(1H-tetrazol-5-yl)-phenyl)-3H-pyrazol-3-one, Mp 248.5° C.

51. From the reaction of 3-pyridylhydrazine and ethylbutyrylacetate, 2,4-dihydro-5-propyl-2-(3-pyridyl)-3H-pyrazol-3-one is obtained. Subsequent reaction with 2-ethylaniline yields 4-(2-ethylanilinomethylene)-2,4-dihydro-5-propyl-2-(3-pyridyl)-3H-pyrazo 1-3-one, Mp 143.9° C.

52. From the reaction of 3-(4-(2-ethylanilinomethylene)-4,5-dihydro-3-methyl-5-oxo-1H-pyrazol-1-yl)-benzonitrile and trimethyltinazide, 4-(2-ethylanilinomethylene)-2,4-dihydro-5-methyl-2-(3-(1H-tetrazol-5-yl)-phenyl)-3H-pyrazol-3-one is obtained, Mp 261.6° C.

53. From the reaction of hydrazinobenzoic acid and ethylacetoacetate, 4-(4,5-dihydro-3-methyl-5-oxo-1H-pyrazol-1-yl)-benzoic acid is obtained. Subsequent reaction with 2-trifluormethylaniline yields 4-(4,5-dihydro-3-methyl-5-oxo-4-(2-trifluormethylanilinomethylene)-1H-pyrazol-1-yl)-benzoic acid, Mp 289.4° C.

54. From the reaction of p-hydrazinobenzoic acid and diethyl-3-oxoglutarate, 4-(3-ethoxycarbonylmethyl-4,5-dihydro-5-oxo-1H-pyrazol-1-yl)-benzoic acid is obtained. Subsequent reaction with 2-ethylaniline yields 4-(4-(2-thylanilinomethylene)-3-ethoxycarbonylmethyl-4,5-dihydro-5-oxo-1H-pyrazol-1-yl)-benzoic acid, Mp 246° C.

55. From the reaction of p-hydrazinobenzoic acid and ethylacetoacetate, 4-(4,5-dihydro-3-methyl-5-oxo-1H-pyrazol-1-yl)-benzoic acid is obtained. Subsequent reaction with 2-(2-propenyloxy)aniline yields 4-(4,5-dihydro-3-methyl-5-oxo-4-(2-(2-propenyloxy)-anilinomethylene)-1H-pyrazol-1-yl)-benzoic acid, Mp 267.9° C.

56. From the reaction of p-hydrazinobenzoic acid and ethylacetoacetate, 4-(4,5-dihydro-3-methyl-5-oxo-1H-pyrazol-1-yl)-benzoic acid is obtained. Subsequent reaction with 2-propoxyaniline yields 4-(4,5-dihydro-3-methyl-5-oxo-4-(2-propoxyanilinomethylene)-1H-pyrazol-1-yl)-benzoic acid, Mp 259.6° C.

57. From the reaction of p-hydrazinobenzoic acid and ethylacetoacetate, 4-(4,5-dihydro-3-methyl-5-oxo-1H-pyrazol-1-yl)-benzoic is obtained. Subsequent reaction with 2-(2-propenyloxy)aniline yields 4-(4,5-dihydro-3-methyl-5-oxo-4-(2-(2-propenyloxy)-anilinomethylene)-1H-pyrazol-1-yl)-benzoic acid, Mp 240.4° C.

58. From the reaction of p-hydrazinobenzoic acid and ethylacetoacetate, 4-(4,5-dihydro-3-methyl-5-oxo-1H-pyrazol-1-yl)-benzoic acid is obtained. Subsequent reaction with 2-methoxyaniline yields 4-(4,5-dihydro-4-(2-methoxyanilinomethylene)-3-methyl-5-oxo-1H-pyrazol-1-yl)-benzoic acid, Mp >300° C.

59. From the reaction of p-hydrazinobenzoic acid and ethylacetoacetate, 4-(4,5-dihydro-3-methyl-5-oxo-1H-pyrazol-1-yl)-benzoic acid is obtained. Subsequent reaction with 2-isopropylaniline yields 4-(4,5-dihydro-4(2-isopropylanilinomethylene)-3-methyl-5-oxo-1H-pyrazol-1-yl)-benzoic acid, Mp 269.5° C.

60. From the reaction of commercially available 3-(4,5-dihydro-3-methyl-5-oxo-1H-pyrazol-1-yl)-benzolsulfonamide and 2-ethylaniline, 3-(4-(2-ethylanilinomethylenaminomethylene)-4,5-dihydro-3-methyl-5-oxo-1H-pyrazol-1-yl)-benzolsulfonamide is obtained, Mp 229.2° C.

61. From the reaction of 2-(1-(4aminophenyl)-4,5-dihydro-5-oxo-1H-pyrazol-3-yl)ethylacetate and trifluorocetanhydride and subsequent reaction with ethylaniline, 2-(4-(2-ethylanilinomethylene)-4,5-dihydro-1-(4-trifluoracetamidophenyl)-5-oxo-1H-pyrazol-3-yl)-ethylacetate is obtained Mp: 197° C.

62. From the reaction of 2-(1-(4-aminophenyl)-4,5-dihydro-5-oxo-1H-pyrazol-3-yl)-ethylacetate and methylchloroformate and subsequent reaction with 2-ethylaniline, 2-(1-(4-methoxycarbonylaminophenyl)-4-((2-ethylanilino)-methylene)-4,5-dihydro-5-oxo-1H-pyrazol-3-yl)-ethylacetate is obtained, Mp: 145° C.

63. From the reaction of 2-(4,5-dihydro-1-(4-aminophenyl)-5-oxo-1H-pyrazol-3-yl)-ethylacetate and methansulfonic acid chloride and subsequent reaction with 2-ethylaniline, 2-(4-((2-ethylanilinomethylene)-4,5-dihydro-1-(4-methanesulfonamidophenyl)-5-oxo-1H-pyrazol-3-yl)-ethylacetate is obtained, Mp: 165° C.

64. From the reaction of 2-(4,5-dihydro-1-(4-aminophenyl)-5-oxo-1H-pyrazol-3-yl)-ethylacetate and acetic acid chloride and subsequent reaction with 2-ethylaniline, 2-(1-(4-acetamidophenyl)-4-((2-ethylanilino)-methylene)-4,5-dihydro-5-oxo-1H-pyrazol-3-yl)-ethylacetate is obtained, Mp: 197° C.

In the same manner the following can be synthesized:

2-(1-(4-(N,N-Diethylsulfamoyl)-phenyl)-4-(2-ethylanilinomethylene)-4,5-dihydro-5-oxo-1H-pyrazol-3-yl)-ethylacetate, Mp: 146° C.

2-(1-(4-(N,N-Diethylsulfamoyl)-phenyl)-4-(2-ethoxyanilinomethylene)-4,5-dihydro-5-oxo-1H-pyrazol-3-yl)-ethylacetate, Mp: 127° C.

2-(1-(4-Acetamidophenyl)-4-(2-ethylanilinomethylene)-4,5-dihydro-5-oxo-1H-pyrazol-3-yl)-ethylacetate, Mp: 194° C.

2-(4-(2-Ethylanilinomethylene)-4,5-dihydro-5-oxo-1-(4-trifluoroacetanido phenyl)-1H-pyrazol-3-yl)-ethylacetate, Mp: 197° C.

2-(4-(2-Ethylanilinomethylene)-4,5-dihydro-1-(4-methoxycarbonylaminophenyl)-5-oxo-1H-pyrazol-3-yl)-ethylacetate, Mp: 144° C.

2-(4-(2-Ethylanilinomethylene)-4,5-dihydro-1-(4-methanesulfonamidophenyl)-5-oxo-1H-pyrazol-3-yl)-ethylacetate, Mp: 165° C.

2-(1-(4-Acetamidophenyl)-4-(2-ethylanilinomethylene)-4,5-dihydro-5-oxo-1H-pyrazol-3-yl)-ethylacetate, Mp: 168° C.

2-(4-(2-Ethylanilinomethylene)-4,5-dihydro-1-(4-methoxycarbonylarninophenyl)-5-oxo-1H-pyrazol-3-yl)-acetic acid Mp: 181° C.

N-(3-(4-(2-Ethylanilinomethylene)-4,5-dihydro-5-oxo-3-propyl-1H-pyrazol-1-yl)-phenyl)-methanesulfonamide Mp: 214° C.

N-(3-(4-(2-Ethylanilinomethylene)-4,5-dihydro-5-oxo-3-propyl-1H-pyrazol-1-yl)-phenyl)-acetamide, Mp: 181° C.

N-(3-(4-(2-Ethylanilinomethylene)-4,5-dihydro-5-oxo-3-propyl-1H-pyrazol-1-yl)-phenyl)-carbamic acid methylester, Mp: 203° C.

2-(4-(2-Ethylanilinomethylene)-4,5-dihydro-5-oxo-1-(3-trifluoroacetamidophenyl)-1H-pyrazol-1-yl)-ethylacetate, Mp: 190° C.

2-(4-(2-Ethylanilinomethylene)-4,5-dihydro-1-(3-methanesulfonamidophenyl)-5-oxo-1H-pyrazol-3-yl)-ethylacetate, Mp: 174° C.

It will be understood that various changes and modifications can be made in the details of procedure, formulation and use without departing from the spirit of the invention, especially as defined in the following claims.

We claim:

1. A method of treating a mammal having precancerous lesions comprising administering a pharmacologically effective amount of a compound of Formula I or pharmaceutically acceptable salt thereof:

wherein $R_1$ is tetrazolyl- or phosphonyl-substituted phenyl, pyridyl, or a substituted or unsubstituted benzyl, phenyl, or 1–3 carbon alkyl chain alkoxybenzyl wherein said substituents on said benzyl, phenyl or alkoxybenzyl are one to three selected from the group consisting of amino, acyl, halogen, nitro, CN, AO—, carboxyl, sulfonyl, A—O—CO, A—CO—NH—, A—CO—NA—, carbamoyl, N-alkylcarbamoyl, 1–6 carbon alkyl chain N,N-dialkylcarbamoyl, A—O—CO—NH—, A—O—CO—NA—, $R_4NSO_2R_5$ and $SO_2NR_4R_5$;

$R_2$ is selected from the group consisting of $C_{1-5}$ alkyl alkoxycarbonylalkyl, hydroxyalkyl and hydroxycarbonylalkyl;

$R_3$ is hydrogen, $C_{1-5}$ alkyl, $C_{1-5}$ alkoxy, halo-substituted alkyl, aminoalkanoyl, aminoalkyl, carbamoyl or $SO_2NR_4R_5$;

$R_4$ and $R_5$ are independently hydrogen or $C_{1-6}$ alkyl, or —$NR_4R_5$ together form a 5 or 6 membered ring optionally containing other heteroatoms selected from the group consisting of N, S, O, and the ring can be optionally substituted by A, A—CO—NH—SO$_2$—, A—CO—NA—SO$_2$, A—SO$_2$—NH—, A—SO$_2$—NA—, (A—SO$_2$)$_2$ N—; and A is $C_{1-6}$ alkyl or $C_{1-6}$ haloalkyl and physiologically acceptable salts thereof.

2. The method according to claim 1 wherein:

$R_2$ is $H_5C_2$—O—CO—CH$_2$, $R_3$ is aminoalkanoyl, aminoalkyl, carbamoyl or $SO_2NR_4R_5$; and $R_4$ and $R_5$ are independently hydrogen or $C_{1-6}$ alky, or —$NR_4R_5$ together form a 5 or 6 membered ring optionally containing other heteroatoms selected from the group consisting of N, S, O, and the ring can be optionally substituted by A; and physiologically acceptable salts thereof.

3. The method of claim 1 wherein said compound is selected from the group consisting of:

N-3-(4-(2-Ethylanilinomethylene)-4,5-dihydro-3-methyl-5-oxo-1H-pyrazol-1-yl)-phenyl)-carbamic acid methylester 4-((2-Ethoxyanilinomethylene)-4,5-dihydro-3-methyl-5-oxo-1H-pyrazol-1-yl)-N-ethylbenzenesulfonamide;

2-(1-4-(N,N-Diethylsulfamoyl)-phenyl)-4-((2-ethylanilino)-methylene)-4,5-dihydro-5-oxo-1H-pyrazol-3-yl)-ethylacetate;

2-(1-4-(N,N-Diethylsulfamoyl)-phenyl)-4-((2-ethoxylanilino)-methylene)-4,5-dihydro-5-oxo-1H-pyrazol-3-yl)-ethylacetate;

2-(1-(4-Acetamidophenyl)-4-((2-ethylanilino)-methylene)-4,5-dihydro-5-oxo-(1H-pyrazol-3-yl)-ethylacetate;

2-(4-((2-Ethylanilino)-methylene)-4,5-dihydro-5-oxo-1-(4-trifluoroacetamidophenyl)-1H-pyrazol-3-yl)-ethylacetate;

2-(1-(4-Ethoxycarbonylaminophenyl)-4-((2-ethylanilino)-methylene)-4,5-dihydro-5-oxo-1H-pyrazol-3-yl)-ethylacetate;

2-(4-((2-Ethylanilinomethylene)-4,5-dihydro-1-(4-methanesulfonamidophenyl)-5-oxo-1H-pyrazol-3-yl)-ethylacetate;

N-(3-(4-(2-Ethylanilinomethylene)-4,5-dihydro-3-methyl-5-oxo-5H-pyrazol-1-yl)-phenyl)-acetamide;

N,N-Diethyl-4-(4-(2-ethylanilinomethylene)-4,5-dihydro-3-methyl-5-oxo-1H-pyrazol-1-yl)-benzenesulfonarmide;

N-Ethyl-4-(4-(2-ethylanilinomethylene)-4,5-dihydro-3-methyl-5-oxo-1H-pyrazol-1-yl)-benzenesulfonamide;

4-(2-Ethoxyanilinomethylene)-2,4-dihydro-5-methyl-2-(4-(4-morpholinylsulfonyl)-phenyl)-3H-pyrazol-3-one;

4-(2-Ethylanilinomethylene)-2,4-dihydro-5-methyl-2-(4-(4-methyl-1-piperinylsulfonyl)-phenyl)-3H-pyrazol-3-one;

N-(3-(4-(2-Ethylanilinomethylene)-4,5-dihydro-3-methyl-5-oxo-1H-pyrarazol-1-yl)-phenyl)-methanesulfonamide;

N-(3-(4-(2-Ethylanilinomethylene)-4,5-dihydro-3-methyl-5-oxo-1H-pyrazol-1-yl)-phenyl)-trifluoroacetamide;

N-(4-(4-(2-Ethylanilinomethylene)-4,5-dihydro-3-methyl-5-oxo-1H-pyrazol-1-yl)-phenyl)-N-methylsulfonylmethansulfonamide;

N,N-Diethyl-4-(4,5-dihydro-4-(2-ethoxyanilinomethylene)-3-methyl-5-oxo-1H-pyrazol-1-yl)-benzenesulfonamide;

N,N-Diethyl-4-(4,5-dihydro-4-(2-methoxyanilinomethylene)-3-methyl-5-oxo-1H-pyrazol-1-yl)-benzenesulfonamide;

3-(4-(2-Ethylanilinomethylene)-4,5-dihydro-5-oxo-3-propyl-1H-pyrazol-1-yl)-benzenesulfonic acid;

4-(4-(2-Ethylanilinomethylene)-4,5-dihydro-5-oxo-3-propyl-1H-pyrazo-1-yl)-benzenesulfonic acid;

2-(4-(2-Ethylanilinomethylene)-4,5-dihydro-1-(4-nitrophenyl)-5-oxo-1H-pyrazol-3-yl)-ethylacetate;

4-(4-(2-Ethylanilinomethylene)-4,5-dihydro-5-oxo-3-propyl-1H-pyrazol-1-yl)-benzoic acid;

4-(4-(2-Ethylanilinomethylene)-4,5-dihydro-3-methyl-5-oxo-1H-pyrazol-1-y 1)-N-hexylbenzamide;

4-(4-(2-Ethylanilinomethylene)-4,5-dihydro-3-methyl-5-oxo-1H-pyrazol-1-y 1)-benzamide;

N,N-Diethyl-4-(4-(2-ethylanilinomethylene)-4,5-dihydro-3-methyl-5-oxo-1H-pyrazol-1-yl)-benzamide;

4-(2-Ethylanilinomethylene-2,4-dihydro-5-propyl-2-(4-pyridyl)-3H-pyrazol-3-one;

N,N-Diethyl-4-(4-(2-ethylanilinomethylene)-4,5-dihydro-5-oxo-3-propyl-1H-pyrazol-1-yl)-benzamide;

4-(4-(2-Ethylanilinomethylene)-4,5-dihydro-5-oxo-3-propyl-1H-pyrazol-1-yl)-N-hexylbenzamide;

4-(4-(2-Ethylanilinomethylene)-4,5-dihydro-5-oxo-3-propyl-1H-pyrazol-1-yl)-benzamide;

4-(2-Ethylanilinomethylene)-2,4-dihydro-5-propyl-2-(4-(1H-tetrazol-5-yl)-phenyl)-3H-pyrazol-3-one;

4-(2-Ethylanilinomethylene)-2,4-dihydro-5-methyl-2-(3-(1H-tetrazol-5-yl)-phenyl)-3H-pyrazol-3-one;

4-(4,5-Dihydro-3-methyl-5-oxo-4-(2-trifluoromethylanilinomethylene)-1H-pyrazol-1-yl)-benzoic acid;

4-(4-(2-Ethylanilinomethylene)-3-ethoxycarbonylmethyl-4,5-dihydro-5-oxo-1H-pyrazol-1-yl)-benzoic acid;

4-(4,5-Dihydro-3-methyl-5-oxo-4-(2-(2-propenyloxy)-anilinomethylene)-1H-pyrazol-1-yl)-benzoic acid;

4-(4,5-Dihydro-3-methyl-5-oxo-4-(2-propoxyanilinomethylene)-1H-pyrazol-1-yl)-benzoic acid;

4-(4,5-Dihydro-4-(2-isopropylanilinomethylene)-3-methyl-5-oxo-1H-pyrazol-1-yl)-benzoic acid;

3-(4-(2-Ethylanilinomethylenaminomethylene)-4,5-dihydro-3-methyl-5-oxo-1H-pyrazol-1-yl)-benzenesulfonamide;

2-(1-(4-Methoxycarbonylaminophenyl)-4-((2-ethylanilino)-methylene)-4,5-dihydro-5-oxo-1H-pyrazol-3-yl)-ethylacetate;

2-(1-(4-(N,N-Diethylsulfamoyl)-phenyl)-4-(2-ethylanilinomethylene)-4,5-dihydro-5-oxo-1H-pyrazol-3-yl)-ethylacetate;

2-(1-(4-(N,N-Diethylsulfamoyl)-phenyl)-4-(2-ethoxyanilinomethylene)-4,5-dihydro-5-oxo-1H-pyrazol-3-yl)-ethylacetate;

2-(1-(4-Acetamidophenyl)-4-(2-ethylanilinomethylene)-4,5-dihydro-5-oxo-1H-pyrazol-3-yl)-ethylacetate;

2-(4-(2-Ethylanilinomethylene)-4,5-dihydro-5-oxo-1-(4-trifluoroacetamido phenyl) 1H-pyrazol-3-yl)-ethylacetate;

2-(4-(2-Ethylanilinomethylene)-4,5-dihydro-1-(4-methoxycarbonylaminophenyl)-5-oxo-1H-pyrazol-3-yl)-ethylacetate;

2-(4-(2-Ethylanilinomethylene)-4,5-dihydro-1-(4-methanesulfonamidophenyl)-5-oxo-1H-pyrazol-3-yl)-ethylacetate;

2-(1-(4-Acetamidophenyl)-4-(2-ethylanilinomethylene)-4,5-dihydro-5-oxo-1H-pyrazol-3-yl)-ethylacetate;

2-(4-(2-Ethylanilinomethylene)-4,5-dihydro-1-(4-methoxycarbonylaminophenyl)-5-oxo-1H-pyrazol-3-yl)-acetic acid;

N-(3-(4-(2-Ethylanilinomethylene)-4,5-dihydro-5-oxo-3-propyl-1H-pyrazol-1-yl)-phenyl)-methanesulfonamide;

N-(3-(4-(2-Ethylanilinomethylene)-4,5-dihydro-5-oxo-3-propyl-1H-pyrazol-1-yl)-phenyl)-acetamide;

N-(3-(4-(2-Ethylanilinomethylene)-4,5-dihydro-5-oxo-3-propyl-1H-pyrazol-1-yl)-phenyl)-carbamic acid methylester;

2-(4-(2-Ethylanilinomethylene)-4,5-dihydro-5-oxo-1-(3-trifluoroacetamidophenyl)-1H-pyrazol-1-yl)-ethylacetate; and 2-(4-(2-Ethylanilinomethylene)-4,5-dihydro-1-(3-methanesulfonamidophenyl)-5-oxo-1H-pyrazol-3-yl)-ethylacetate.

4. A method for inhibiting the growth of neoplastic cells comprising exposing the cells to a growth inhibiting effective amount of a compound of Formula I or pharmaceutically acceptable salt thereof, wherein $R_1$ is tetrazolyl- or phosphonyl-substituted phenyl, pyridyl, or a substituted or unsubstituted benzyl, phenyl, or 1–3 carbon alkyl chain alkoxybenzyl wherein said substituents on said benzyl, phenyl or alkoxybenzyl are one to three selected from the group consisting of amino, acyl, halogen, nitro, CN, AO—, carboxyl, sulfonyl, A—O—CO, A—CO—NH—, A—CO—NA—, carbamoyl, N-alkylcarbamoyl, 1–6 carbon alkyl chain N,N-dialkylcarbamoyl, A—O—CO—NH—, A—O—CO—NA—, $R_4NSO_2R_5$ and $SO_2NR_4R_5$;

$R_2$ is selected from the group consisting of $C_{1-5}$ alkyl, alkoxycarbonylalkyl, hydroxyalkyl and hydroxycarbonylalkyl;

$R_3$ is hydrogen, $C_{1-5}$ alkyl, $C_{1-5}$ alkoxy, halo-substituted alkyl, aminoalkanoyl, aminoalkyl, carbamoyl or $SO_2NR_4R_5$;

$R_4$ and $R_5$ are independently hydrogen or $C_{1-6}$ alkyl, or —$NR_4R_5$ together form a 5 or 6 membered ring optionally containing other heteroatoms selected from the group consisting of N, S, O, and the ring can be optionally substituted by A, A—CO—NH—$SO_2$—, A—CO—NA—$SO_2$, A—$SO_2$—NH—, A—$SO_2$—NA—, $(A-SO_2)_2$ N—; and A is $C_{1-6}$ alkyl or $C_{1-6}$ haloalkyl and physiologically acceptable salts thereof.

5. The method according to claim 4 wherein:

$R_2$ is $H_5C_2$—O—CO—$CH_2$, $R_3$ is aminoalkanoyl, aminoalkyl, carbamoyl or $SO_2NR_4R_5$; and $R_4$ and $R_5$ are independently hydrogen or $C_{1-6}$ alkyl, or —$NR_4R_5$ together form a 5 or 6 membered ring optionally containing other heteroatoms selected from the group consisting of N, S, O, and the ring can be optionally substituted by A; and physiologically acceptable salts thereof.

6. The method of claim 4 wherein said compound is selected from the group consisting of:

N-3-(4-(2-Ethylanilinomethylene)-4,5-dihydro-3-methyl-5-oxo-1H-pyrazol-1-yl)-phenyl)-carbamic acid methylester;

4-((2-Ethoxyanilinomethylene)-4,5-dihydro-3-methyl-5-oxo-1H-pyrazol-1-yl)-N-ethylbenzenesulfonamide;

2-(1-4-(N,N-Diethylsulfamoyl)-phenyl)-4-((2-ethylanilino)-methylene)-4,5-dihydro-5-oxo-1H-pyrazol-3-yl)-ethylacetate;

2-(1-4-(N,N-Diethylsulfamoyl)-phenyl)-4-((2-ethoxylanilino)-methylene)-4,5-dihydro-5-oxo-1H-pyrazol-3-yl)-ethylacetate;

2-(1-(4-Acetamidophenyl)-4-((2-ethylanilino)-methylene)-4,5-dihydro-5-oxo-1H-pyrazol-3-yl)-ethylacetate;

2-(4-((2-Ethylanilino)-methylene)-4,5-dihydro-5-oxo-1-(4-trifluoroacetamidophenyl)-1H-pyrazol-3-yl)-ethylacetate;

2-(1-(4-Ethoxycarbonylaminophenyl)-4-((2-ethylanilino)-methylene)-4,5-dihydro-5-oxo-1H-pyrazol-3-yl)-ethylacetate;

2-(4-((2-Ethylanilinomethylene)-4,5-dihydro-1-(4-methanesulfonamnidophenyl)-5-oxo-1H-pyrazol-3-yl)-ethylacetate;

N-(3-(4-(2-Ethylanilinomethylene)-4,5-dihydro-3-methyl-5-oxo-5H-pyrazol-1-yl)-phenyl)-acetamide;

N,N-Diethyl-4-(4-(2-ethylanilinomethylene)-4,5-dihydro-3-methyl-5-oxo-1H-pyrazol-1-yl)-benzenesulfonamide;

N-Ethyl-4-(4-(2-ethylanilinomethylene)-4,5-dihydro-3-methyl-5-oxo-1H-pyrazol-1-yl)-benzenesulfonamide;

4-(2-Ethoxyanilinomethylene)-2,4-dihydro-5-methyl-2-(4-(4-morpholinylsulfonyl)-phenyl)-3H-pyrazol-3-one;

4-(2-Ethylanilinomethylene)-2,4-dihydro-5-methyl-2-(4-(4-methyl-1-piperinylsulfonyl)-phenyl)-3H-pyrazol-3-one;

N-(3-(4-(2-Ethylanilinomethylene)-4,5-dihydro-3-methyl-5-oxo-1H-pyrazol-1-yl)-phenyl)-methanesulfonamide;

N-(3-(4-(2-Ethylanilinomethylene)-4,5-dihydro-3-methyl-5-oxo-1H-pyrazol-1-yl)-phenyl)-trifluoroacetamide;

N-(4-(4-(2-Ethylanilinomethylene)-4,5-dihydro-3-methyl-5-oxo-1H-pyrazol-1-yl)-phenyl)-N-methylsulfonylmethansulfonamide;

N,N-Diethyl-4-(4,5-dihydro-4-(2-ethoxyanilinomethylene)-3-methyl-5-oxo-1H-pyrazol-1-yl)-benzenesulfonamide;

N,N-Diethyl4-(4,5-dihydro-4-(2-methoxyanilinomethylene)-3-methyl-5-oxo-1H-pyrazol-1-yl)-benzenesulfonamide;

3-(4-(2-Ethylanilinomethyene)-4,5-dihydro-5-oxo-3-propyl-1H-pyrazol-1-yl)-benzenesulfonic acid;

4-(4-(2-Ethylanilinomethylene)-4,5-dihydro-5-oxo-3-propyl-1H-pyrazol-1-yl)-benzenesulfonic acid;

2-(4-(2-Ethylanilinomethylene)-4,5-dihydro-1-(4-nitrophenyl)-5-oxo-1H-pyrazol-3-yl)-ethylacetate;

4-(4-(2-Ethylanilinomethylene)-4,5-dihydro-5-oxo-3-propyl-1H-pyrazol-1-yl)-benzoic acid;

4-(4-(2-Ethylanilinomethylene)-4,5-dihydro-3-methyl-5-oxo-1H-pyrazol-1-yl)-N-hexylbenzamide;

4-(4-(2-Ethylanilinomethylene)-4,5-dihydro-3-methyl-5-oxo-1H-pyrazol-1-yl)-benzamide;

N,N-Diethyl-4-(4-(2-ethylanilinomethylene)-4,5-dihydro-3-methyl-5-oxo-1H-pyrazol-1-yl)-benzamide;

4-(2-Ethylanilinomethylene-2,4-dihydro-5-propyl-2-(4-pyridyl)-3H-pyrazol-3-one;

N,N-Diethyl-4-(4-(2-ethylanilinomethylene)-4,5-dihydro-5-oxo-3-propyl-1H-pyrazol-1-yl)-benzamide;

4-(4-(2-Ethylanilinomethylene)-4,5-dihydro-5-oxo-3-propyl-1H-pyrazol-1-yl)-N-hexylbenzamide;

4-(4-(2-Ethylanilinomethylene)-4,5-dihydro-5-oxo-3-propyl-1H-pyrazol-1-yl)-benzamide;

4-(2-Ethylanilinomethylene)-2,4-dihydro-5-propyl-2-(4-(1H-tetrazol-5-yl)-phenyl)-3H-pyrazol-3-one;

4-(2-Ethylanilinomethylene)-2,4-dihydro-5-methyl-2-(3-(1H-tetrazol-5-yl)-phenyl)-3H-pyrazol-3-one;

4-(4,5-Dihydro-3-methyl-5-oxo-4-(2-trifluoromethylanilinomethylene)-1H-pyrazol-1-yl)-benzoic acid;

4-(4-(2-Ethylanilinomethylene)-3-ethoxycarbonylmethyl-4,5-dihydro-5-oxo-1H-pyrazol-1-yl)-benzoic acid;

4-(4,5-Dihydro-3-methyl-5-oxo-4-(2-(2-propenyloxy)-anilinomethylene)-1H-pyrazol-1-yl)-benzoic acid;

4-(4,5-Dihydro-3-methyl-5-oxo-4-(2-propoxyanilinomethylene)-1H-pyrazol-1-yl)-benzoic acid;

4-(4,5-Dihydro-4-(2-isopropylanilinomethylene)-3-methyl-5-oxo-1H-pyrazol-1-yl)-benzoic acid;

3-(4-(2-Ethylanilinomethyleneaminomethylene)-4,5-dihydro-3-methyl-5-oxo-1H-pyrazol-1-yl)-benzenesulfonamide;

2-(1-(4-Methoxycarbonylaminophenyl)-4-((2-ethylanilino)-methylene)-4,5-dihydro-5-oxo-1H-pyrazol-3-yl)-ethylacetate;

2-(1-(4-(N,N-Diethylsulfamoyl)-phenyl)-4-(2-ethylanilinomethylene)-4,5-dihydro-5-oxo-1H-pyrazol-3-yl)-ethylacetate;

2-(1-(4-(N,N-Diethylsulfamoyl)-phenyl)-4-(2-ethoxyanilinomethylene)-4,5-dihydro-5-oxo-1H-pyrazol-3-yl)-ethylacetate;

2-(1-(4-Acetamidophenyl)4-(2-ethylanilinomethylene)-4,5-dihydro-5-oxo-1H-pyrazol-3-yl)-ethylacetate;

2-(4-(2-Ethylanilinomethylene)-4,5-dihydro-5-oxo-1-(4-trifluoroacetamido phenyl)-1H-pyrazol-3-yl)-ethylacetate;

2-(4-(2-Ethylanilinomethylene)-4,5-dihydro-1-(4-methoxycarbonylaminophenyl)-5-oxo-1H-pyrazol-3-yl)-ethylacetate;

2-(4-(2-Ethylanilinomethylene)-4,5-dihydro-1-(4-methanesulfonamidophenyl)-5-oxo-1H-pyrazol-3-yl)-ethylacetate;

2-(1-(4-Acetamidophenyl)-4-(2-ethylanilinomethylene)-4,5-dihydro-5-oxo-1H-pyrazol-3-yl)-ethylacetate;

2-(4-(2-Ethylanilinomethylene)-4,5-dihydro-1-(4-methoxycarbonylaminophenyl)-5-oxo-1H-pyrazol-3-yl)-acetic acid;

N-(3-(4-(2-Ethylanilinomethylene)-4,5-dihydro-5-oxo-3-propyl-1H-pyrazol-1-yl)-phenyl)-methanesulfonamide;

N-(3-(4-(2-Ethylanilinomethylene)-4,5-dihydro-5-oxo-3-propyl-1H-pyrazol-1-yl)-phenyl)-acetamide;

N-(3-(4-(2-Ethylanilinomethylene)-4,5-dihydro-5-oxo-3-propyl-1H-pyrazol-1-yl)-phenyl)-carbamic acid methylester;

2-(4-(2-Ethylanilinomethylene)-4,5-dihydro-5-oxo-1-(3-trifluoroacetamidophenyl)-1H-pyrazol-1-yl)-ethylacetate;

2-(4-(2-Ethylanilinomethylene)-4,5-dihydro-1-(3-methanesulfonamidophenyl)-5-oxo-1H-pyrazol-3-yl)-ethylacetate.

7. A method for regulating apoptosis in human cells comprising exposing said cells to an effective amount of a compound of the formula:

wherein $_R$ is tetrazolyl- or phosphonyl-substituted phenyl, pyridyl, or a substituted or unsubstituted benzyl, phenyl, or 1–3 carbon alkyl chain alkoxybenzyl wherein said substituents on said benzyl, phenyl or alkoxybenzyl are one to three selected from the group consisting of amino, acyl, halogen, nitro, CN, AO—, carboxyl, sulfonyl, A—O—CO, A—CO—NH—, A—CO—NA—, carbamoyl, N-alkylcarbamoyl, 1–6 carbon alkyl chain N,N-dialkylcarbamoyl, A—O—CO—NH—, A—O—CO—NA—, $R_4NSO_2R_5$ and $SO_2NR_4R_5$;

$R_2$ is selected from the group consisting of $C_{1-6}$ alkyl, alkoxycarbonylalkyl, hydroxyalkyl and hydroxycarbonylalkyl;

$R_3$ is hydrogen, $C_{1-5}$ alkyl, $C_{1-5}$ alkoxy, halo-substituted alkyl, aminoalkanoyl, aminoalkyl, carbamoyl or $SO_2NR_4R_5$;

$R_4$ and $R_5$ are independently hydrogen or $C_{1-6}$ alkyl, or —$NR_4R_5$ together form a 5 or 6 membered ring optionally containing other heteroatoms selected from the group consisting of N, S, O, and the ring can be optionally substituted by A, A—CO—NH—$SO_2$—, A—CO—NA—$SO_2$, A—$SO_2$—NH—, A—$SO_2$—NA—, (A—$SO_2$)$_2$ N—; and A is $C_{1-6}$ alkyl or $C_{1-6}$ haloalkyl and physiologically acceptable salts thereof.

8. The method according to claim 7 wherein:

$R_2$ is $H_5C_2$—O—CO—$CH_2$, $R_3$ is aminoalkanoyl, aminoalkyl, carbamoyl or $SO_2NR_4R_5$; and $R_4$ and $R_5$ are independently hydrogen or $C_{1-6}$ alkyl, or —$NR_4R_5$ together form a 5 or 6 membered ring optionally containing other heteroatoms selected from the group consisting of N, S, O, and the ring can be optionally substituted by A; and physiologically acceptable salts thereof.

9. The method of claim 7 wherein said compound is selected from the group consisting of:

N-3-(4-(2-Ethylanilinomethylene)-4,5-dihydro-3-methyl-5-oxo-1H-pyrazol-1-yl)-phenyl)-carbamic acid methylester;

4-((2-Ethoxyanilinomethylene)-4,5-dihydro-3-methyl-5-oxo-1H-pyrazol-1-yl)-N-ethylbenzenesulfonamide;

2-(1-4-(N,N-Diethylsulfamoyl)-phenyl)-4-((2-ethylanilino)-methylene)-4,5-dihydro-5-oxo-1H-pyrazol-3-yl)-ethylacetate;

2-(1-4-(N,N-Diethylsulfamoyl)-phenyl)-4-((2-ethoxylanilino)-methylene)-4,5-dihydro-5-oxo-1H-pyrazol-3-yl)-ethylacetate 2-(1-(4-Acetamidophenyl)-4-((2-ethylanilino)-methylene)-4,5-dihydro-5-oxo-1H-pyrazol-3-yl)-ethylacetate;

2-(4-((2-Ethylanilino)-methylene)-4,5-dihydro-5-oxo-1-(4-trifluoroacetamidophenyl)-1H-pyrazol-3-yl)-ethylacetate;

2-(1-(4-Ethoxycarbonylaminophenyl)-4-((2-ethylanilino)-methylene)-4,5-dihydro-5-oxo-1H-pyrazol-3-yl)-ethylacetate;

2-(4-((2-Ethylanilinomethylene)-4,5-dihydro-1-(4-methanesulfonamidophenyl)-5-oxo-1H-pyrazol-3-yl)-ethylacetate;

N-(3-(4-(2-Ethylanilinomethylene)-4,5-dihydro-3-methyl-5-oxo-5H-pyrazol-1-yl)-phenyl)-acetamide;

N,N-Diethyl-4-(4-(2-ethylanilinomethylene)-4,5-dihydro-3-methyl-5-oxo-1H-pyrazol-1-yl)-benzenesulfonamide;

N-Ethyl-4-(4-(2-ethylanilinomethylene)-4,5-dihydro-3-methyl-5-oxo-1H-pyrazol-1-yl)-benzenesulfonamide;

4-(2-Ethoxyanilinomethylene)-2,4-dihydro-5-methyl-2-(4-(4-morpholinylsulfonyl)-phenyl)-3H-pyrazol-3-one;

4-(2-Ethylanilinomethylene)-2,4-dihydro-5-methyl-2-(4-(4-methyl-1-piperinylsulfonyl)-phenyl)-3H-pyrazol-3-one;

N-(3-(4-(2-Ethylanilinomethylene)-4,5-dihydro-3-methyl-5-oxo-1H-pyrazol-1-yl)-phenyl)-methanesulfonamide;

N-(3-(4-(2-Ethylanilinomethylene)-4,5-dihydro-3-methyl-5-oxo-1H-pyrazol-1-yl)-phenyl)-trifluoroacetamide;

N-(4-(4-(2-Ethylanilinomethylene)-4,5-dihydro-3-methyl-5-oxo-1H-pyrazol-1-yl)-phenyl)-N-methylsulfonylmethansulfonamide;

N,N-Diethyl-4-(4,5-dihydro-4-(2-ethoxyanilinomethylene)-3-methyl-5-oxo-1H-pyrazol-1-yl)-benzenesulfonamide;

N,N-Diethyl-4-(4,5-dihydro-4-(2-methoxyanilinomethylene)-3-methyl-5-oxo-1H-pyrazol-1-yl)-benzenesulfonamide;

3-(4-(2-Ethylanilinomethylene)-4,5-dihydro-5-oxo-3-propyl-1H-pyrazol-1-yl)-benzenesulfonic acid;

4-(4-(2-Ethylanilinomethylene)-4,5-dihydro-5-oxo-3-propyl-1H-pyrazol-1-yl)-benzenesulfonic acid;

2-(4-(2-Ethylanilinomethylene)-4,5-dibydro-1-(4-nitrophenyl)-5-oxo-1H-pyrazol-3-yl)-ethylacetate;

4-(4-(2-Ethylanilinomethylene)-4,5-dihydro-5-oxo-3-propyl-1H-pyrazol-1-yl)-benzoic acid;

4-(4-(2-Ethylanilinomethylene)-4,5-dihydro-3-methyl-5-oxo-1H-pyrazol-1-yl)-N-hexylbenzamide;

4-(4-(2-Ethylanilnomethylene)-4,5-dihydro-3-methyl-5-oxo-1H-pyrazol-1-yl)-benzamide;

N,N-Diethyl-4-(4-(2-ethylanilinomethylene)-4,5-dihydro-3-methyl-5-oxo-1H-pyrazol-1-yl)-benzamide;

4-(2-Ethylanilinomethylene-2,4-dihydro-5-propyl-2-(4-pyridyl)-3H-pyrazol-3-one

N,N-Diethyl-4-(4-(2-ethylanilinomethylene)-4,5-dihydro-5-oxo-3-propyl-1H-pyrazol-1-yl)-benzamide;

4-(4-(2-Ethylanilinomethylene)-4,5-dihydro-5-oxo-3-propyl-1H-pyrazol-1-yl)-N-hexylbenzamide;

4-(4-(2-Ethylanilinomethylene)-4,5-dihydro-5-oxo-3-propyl-1H-pyrazol-1-yl)-benzamide;

4-(2-Ethylanilinomethylene)-2,4-dihydro-5-propyl-2-(4-(1H-tetrazol-5-yl)-phenyl)-3H-pyrazol-3-one;

4-(2-Ethylanilinomethylene)-2,4-dihydro-5-methyl-2-(3-(1H-tetrazol-5-yl)-phenyl)-3H-pyrazol-3-one;

4-(4,5-Dihydro-3-methyl-5-oxo-4-(2-trifluoromethylanilinomethylene)-1H-pyrazol-1-yl)-benzoic acid;

4-(4-(2-Ethylanilinomethylene)-3-ethoxycarbonylmethyl-4,5-dihydro-5-oxo-1H-pyrazol-1-yl)-benzoic acid;

4-(4,5-Dihydro-3-methyl-5-oxo-4-(2-(2-propenyloxy)-anilinomethylene)-1H-pyrazol-1-yl)-benzoic acid;

4-(4,5-Dihydro-3-methyl-5-oxo-4-(2-propoxyanilinomethylene)-1H-pyrazol-1-yl)-benzoic acid;

4-(4,5-Dihydro-4-(2-isopropylanilinomethylene)-3-methyl-5-oxo-1H-pyrazol-1-yl)-benzoic acid;

3-(4-(2-Ethylanilinomethylenaminomethylene)-4,5-dihydro-3-methyl-5-oxo-1H-pyrazol-1-yl)-benzenesulfonamide;

2-(1-(4-Methoxycarbonylaminophenyl)-4-((2-ethylanilino)-methylene)-4,5-dihydro-5-oxo-1H-pyrazol-3-yl)-ethylacetate;

2-(1-(4-(N,N-Diethylsulfamoyl)-phenyl)-4-(2-ethylanilinomethylene)-4,5-dihydro-5-oxo-1H-pyrazol-3-yl)-ethylacetate;

2-(1-(4-(N,N-Diethylsulfamoyl)-phenyl)-4-(2-ethoxyanilinomethylene)-4,5-dihydro-5-oxo-1H-pyrazol-3-yl)-ethylacetate;

2-(1-(4-Acetamidophenyl)-4-(2-ethylanilinomethylene)-4,5-dihydro-5-oxo-1H-pyrazol-3-yl)-ethylacetate;

2-(4-(2-Ethylanilinomethylene)-4,5-dihydro-5-oxo-1-(4-trifluoroacetamnido phenyl)(1H-pyrazol-3-yl)-ethylacetate;

2-(4-(2-Ethylanilinomethylene)-4,5-dihydro-1-(4-methoxycarbonylaminophenyl)-5-oxo-1H-pyrazol-3-yl)-ethylacetate;

2-(4-(2-Ethylanilinomethylene)-4,5-dihydro-1-(4-methanesulfonamidophenyl)-5-oxo-1H-pyrazol-3-yl)-ethylacetate;

2-(1-(4-Acetamidophenyl)-4-(2-ethylanilinomethylene)-4,5-dihydro-5-oxo-1H-pyrazol-3-yl)-ethylacetate;

2-(4-(2-Ethylanilinomethylene)-4,5-dihydro-1-(4-methoxycarbonylaminophenyl)-5-oxo-1H-pyrazol-3-yl)-acetic acid;

N-(3-(4-(2-Ethylanilinomethylene)-4,5-dihydro-5-oxo-3-propyl-1H-pyrazol-1-yl)-phenyl)-methanesulfonamide;

N-(3-(4-(2-Ethylanilinomethylene)-4,5-dihydro-5-oxo-3-propyl-1H-pyrazol-1-yl)-phenyl)-acetamide;

N-(3-(4-(2-Ethylanilinomethylene)-4,5-dihydro-5-oxo-3-propyl-1H-pyrazol-1-yl)-phenyl)-carbamic acid methylester;

2-(4-(2-Ethylanilinomethylene)-4,5-dihydro-5-oxo-1-(3-trifluoroacetamidophenyl)-1H-pyrazol-1-yl)-ethylacetate; and 2-(4-(2-Ethylanilinomethylene)-4,5-dihydro-1-(3-methanesulfonamidophenyl)-5-oxo-1H-pyrazol-3-yl)-ethylacetate.

\* \* \* \* \*